United States Patent [19]
Richichi et al.

[11] Patent Number: 5,438,655
[45] Date of Patent: Aug. 1, 1995

[54] METHODS AND APPARATUS FOR UPDATING AND ANTIALIASING WAVEFORMS

[75] Inventors: Frank Richichi, Bedford; Jeffrey T. LeBlanc, Belmont, both of Mass.

[73] Assignee: Hewlett-Packard Company, Palo Alto, Calif.

[21] Appl. No.: 99,024

[22] Filed: Jul. 29, 1993

[51] Int. Cl.⁶ .............................................. G06F 15/62
[52] U.S. Cl. ................................................. 395/142
[58] Field of Search ................ 395/142, 143, 140, 141, 395/161; 345/24, 133, 134, 135, 136

[56] References Cited

U.S. PATENT DOCUMENTS 5,371,842 12/1994 Easton et al. ...................... 395/140

OTHER PUBLICATIONS

Bresenham, J. E. 1965 "Algorithm For Computed Control of Digital Plotter" IBM Systems Journal 4:25–30.

*Primary Examiner*—Phu K. Nguyen

[57] ABSTRACT

A method and apparatus for scheduling waveform updates, and for implementing antialiasing techniques compatible with a standard graphics drawing package. Interrupts are requested at regular intervals to update a waveform based on data samples received from a data source. When there is a delay in servicing a requested interrupt, the waveform is updated with a relatively large number of data samples so that the monitoring system does not fall behind the data source. However, a limit is placed on the number of data samples used to update the waveform at the servicing of a single interrupt to ensure that an erase bar that updates the waveform maintains a substantially constant velocity. Additionally, when there is a delay in servicing an interrupt, the next interrupt is requested to occur more quickly. The waveform is broken up into a plurality of wave segments extending between adjacent pixel columns and each wave segment is updated using three calls to a line drawing primitive of the graphics package. Two one-pixel wide lines are drawn in an intermediate antialiasing color, and a one-pixel wide line is drawn in a foreground color.

38 Claims, 10 Drawing Sheets

|  | 7 WAVES | 12 WAVES | 16 WAVES |
|---|---|---|---|
| X SERVER | 14% | 20% | 22% |
| USER APPLICATION | 4% | 5% | 5% |

Fig. 8a

|  | 7 WAVES | 12 WAVES | 16 WAVES |
|---|---|---|---|
| X SERVER | 51% | 84% | 90% |
| USER APPLICATION | 4% | 5% | 5% |

Fig. 8b

|  | 7 WAVES | 12 WAVES | 16 WAVES |
|---|---|---|---|
| X SERVER | 8% | 13% | 15% |
| USER APPLICATION | 18% | 36% | 38% |

Fig. 8c

|  | 7 WAVES | 12 WAVES | 16 WAVES |
|---|---|---|---|
| X SERVER | 20% | 30% | 36% |
| USER APPLICATION | 6% | 7% | 8% |

Fig. 8d

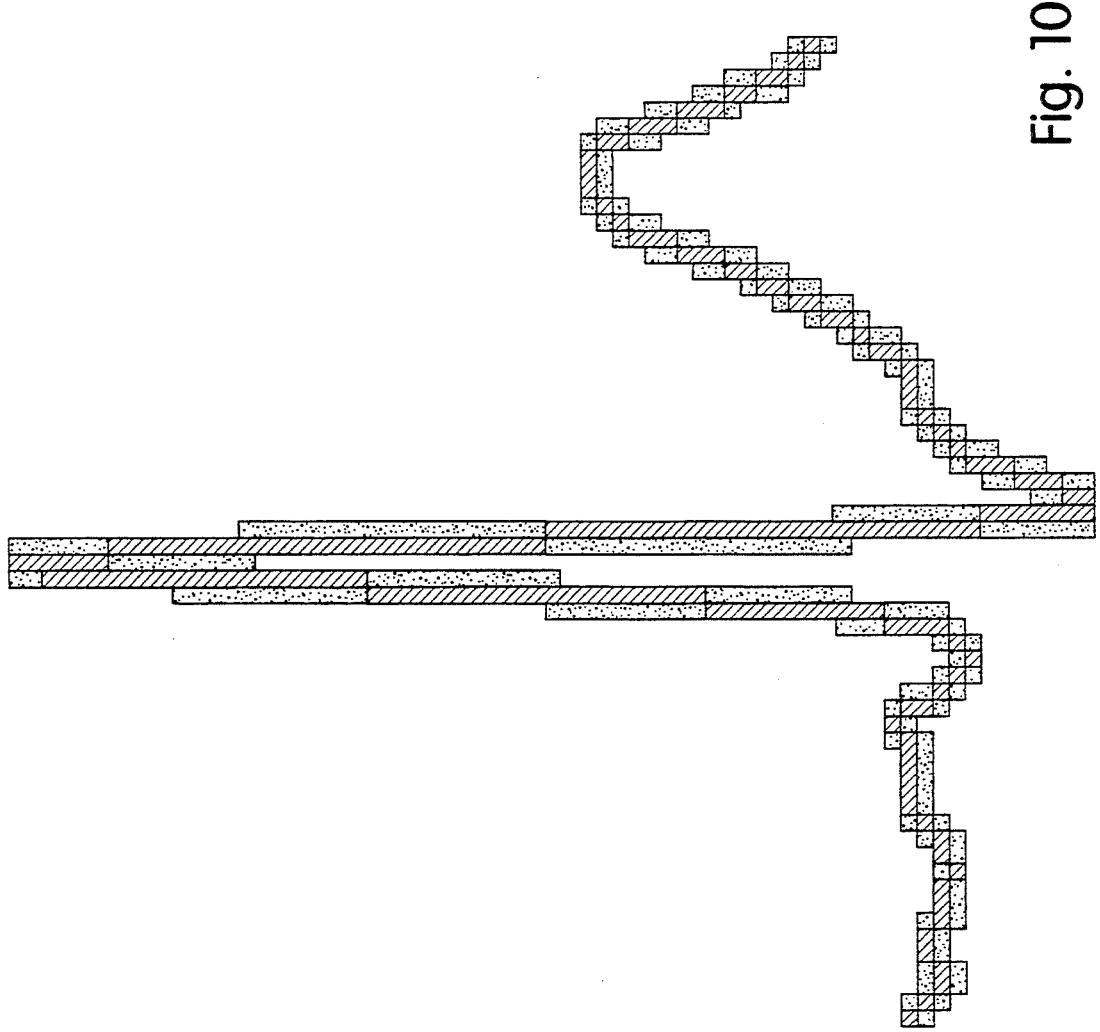

METHODS AND APPARATUS FOR UPDATING AND ANTIALIASING WAVEFORMS

FIELD OF THE INVENTION

This invention relates to a monitoring system for displaying waveforms that each represent the time-varying characteristics of a data source, such as a physiological condition of a medical patient. More particularly, this invention provides methods and apparatus for scheduling the updating of waveforms on a monitoring system, and for implementing antialiasing techniques compatible with a standard graphics drawing package such as X Windows.

BACKGROUND OF THE INVENTION

Monitoring systems have been developed for displaying waveforms that represent the manner in which a data source varies over time. For example, monitoring systems have been developed that utilize a display device such as a cathode ray tube (CRT) for displaying waveforms representing the manner in which various physiological conditions of a medical patient vary over time. More specifically, monitoring systems have been developed for displaying waveforms indicating the manner in which a patient's blood pressure varies over time, as well as for displaying a patient's electrocardiogram.

An electrocardiogram (hereafter ECG) is a waveform which indicate the manner in which a voltage measured across a patient's heart varies with time. Heart voltages can change rapidly and therefore, typical monitoring systems for generating an ECG record a data sample indicating the heart's voltage every 2 ms. In this manner, the monitoring system samples an analog voltage signal generated by the patient and converts signal into digital data that is recorded as a plurality of discrete data samples. In order to accurately represent the manner in which the patient's heart condition varies over time, every recorded data sample need not be displayed. Therefore, decimation algorithms have been developed that select a subset of the recorded data samples which are representative of the way in which the patient's heart condition varies over a given period of time. In this manner, the number of data samples displayed is reduced from the number of data samples received from the data source.

Historically, prior art ECG monitoring systems utilize display screens having one hundred twenty-five pixels per inch and update one inch of the display screen every second. Therefore, for ECG data that is sampled at 500 Hz, the decimation algorithms typically reduce the number of data samples received by a factor of four prior to display. The prior art ECG monitoring systems typically update the waveform displayed on the display device every 32 ms. During each 32 ms time period between waveform updates, sixteen data samples are received from the patient. The decimation algorithms typically reduce the sixteen data samples during each 32 ms update period to four representative data samples for display on the display device. Therefore, prior art ECG monitoring systems typically update the waveform with four data samples (represented by four pixels) every 32 ms.

As can be seen from the foregoing, prior art ECG monitoring systems typically update the display device on a frequent basis (every 32 ms), and consistently update the waveform at this frequency within a small margin of error (e.g. ±2 ms). In this manner, these systems essentially maintain a synchronized lock-step relationship with the data source with little latency or buffering so that when a sample of data is received, it is quickly displayed.

Monitoring systems typically utilize a fixed wave to represent the time-varying characteristics of the data source. FIGS. 1(a) and 1(b) illustrate the manner in which a fixed wave is displayed on a display device 3. An erase bar 5 shown in dotted line moves across the display device 3 in a left to right direction and separates the waveform into a lefthand portion 4 and a righthand portion 6. As new data samples are received and used as a basis for updating the display device, the erase bar 5 moves across the display device, erasing the previously displayed portion of the waveform and updating the waveform to represent the most recently received data samples. When the erase bar 5 reaches the right side of the display device 3, it wraps around and returns to the left side.

To update the waveform with the above-described frequency and consistency, prior art monitoring systems typically use proprietary real-time operating systems that support short process swap and interrupt latencies, as well as regular and precise scheduling of tasks. The use of real-time operating systems enables the prior art monitoring systems to operate in a lock-step manner whereby the waveform is updated at consistent intervals, and with the same amount of data for each update. As a result, the erase bar moves across the display screen with a constant velocity. Maintaining the movement of the erase bar at a constant velocity is desirable because if the erase bar moved across the screen in a jerky manner, it could distract the user and would be aesthetically unpleasing. In order to operate in the above-described lock-step manner, interrupt requests for updating the waveform are given high priority so that they are promptly serviced by the operating system. As a result, the processor is repeatedly interrupted from other processing tasks in order to update the waveform.

It is desirable to develop a real-time monitoring system that includes a waveform update scheduler which operates in a manner that does not require that interrupts for updating the waveform be assigned high priority.

It is also desirable to develop a monitoring system that can be implemented with industry standard hardware and software, and with an industry standard operating system. However, some industry standard operating systems such as UNIX (UNIX is a registered trademark of AT&T in the USA and other countries) do not operate on a real-time basis because they do not support short process swap and interrupt latencies, or precise task scheduling. Therefore, the above-described monitoring systems that update the waveform by maintaining a lock-step relationship with the data source could not be implemented on a system having a non-real time operating system such as UNIX. Since non-real time operating systems do not support the scheduling of regular and precise interrupts, a monitoring system employing such an operating system could not ensure that the display device would be regularly updated when requested, because delays would be experienced in servicing some interrupts, resulting in delays between waveform updates. As a result, the waveform would not be smoothly updated because the erase bar would move in a jerky manner and would not maintain a constant velocity.

It is also desirable to develop a method of scheduling waveform updates on a real-time monitoring system so that interrupts for updating the waveform are not required to be assigned high priority, thereby providing flexibility for the system to process other high priority tasks In addition to updating waveforms on a regular and consistent basis, prior art monitoring systems also employ antialiasing techniques to draw the waveforms in a smooth manner. When waveforms are drawn on a display device, the waveform is drawn in a foreground color and the remainder of the screen is drawn in a background color that is sufficiently different from the foreground color so that the waveform can be seen. If the screen is drawn using only two colors, each pixel on the display screen must necessarily be assigned to either the foreground or background color. As a result, an undesirable effect known as aliasing occurs wherein the waveform, as shown for example in FIG. 2, has a stair-step or jagged look. Antialiasing techniques have been developed to reduce the jagged look of the waveform by using colors intermediate to the foreground and background colors to soften the waveform's transition edges. However, because monitoring systems have typically been implemented using proprietary hardware and software, antialiasing techniques have not been developed for use with standard graphics tool sets, such as the X Window System.

SUMMARY OF THE INVENTION

The foregoing problems are solved in one illustrative embodiment of the invention in which a method and apparatus are provided for operating a monitoring system that displays a waveform representing a time-varying characteristic of a data source. The monitoring system includes a processor executing an operating system, a memory and a display device having a plurality of pixels. The display device displays the waveform as a fixed wave with an erase bar moving across the display screen to udpate the waveform. In accordance with the invention, requests are made that the operating system service an interrupt after the expiration of an interrupt time period, and data samples received from the data source are stored in the memory. A maximum number of stored data samples that will be used to update the waveform at the servicing of a single interrupt is determined to ensure that the erase will maintain a substantially constant velocity as it moves across the display device. When the requested interrupt is serviced, a determination is made as to whether the number of stored data samples exceeds the maximum number and the waveform is updated. When the number of stored data samples exceeds the maximum number, the waveform is updated based on only the maximum number of data samples.

In another illustrative embodiment of the invention, determinations are made as to an ideal interrupt time period and a corresponding ideal number of data samples. The ideal interrupt time period indicates a time period at which the waveform would ideally be updated to synchronize waveform updates with the data source, and the ideal number of data samples indicates the number of data samples that will be received from the data source during each ideal interrupt time period. A request is made that the operating system service an interrupt after the expiration of the ideal interrupt time period and the data samples received from the data source prior to the servicing of the interrupt are stored in the memory. When the interrupt is serviced, a determination is made as to the time at which the next data sample to be updated to the display device was received. Thereafter, an update time period is determined which indicates the amount of time elapsed between the receipt of the next data sample to be updated and the time at which the interrupt was serviced. A determination is made as to whether the update time period is two or more times as long as the ideal interrupt time period and when it is, the waveform is updated with more than the ideal number of data samples, and when it is not, the waveform is updated based on the ideal number of data samples. A difference between the time at which the interrupt was requested to be serviced and the time at which it was actually serviced is determined, the difference indicating an interrupt lag period. The requested interrupt time period is reduced by the lag time period and another interrupt is requested.

In another illustrative embodiment of the invention, an ideal interrupt time period is determined which indicates a time period at which waveform updates would ideally be performed to synchronize the waveform updates with the receipt of the data samples. A request is made that the operating system service an interrupt after the expiration of the ideal interrupt time period and the received data samples are stored in the memory. When the requested interrupt is serviced, the waveform is updated based on at least some of the stored data samples. A difference between the time at which the interrupt was requested to be serviced and the time it which it was actually serviced is determined, the difference indicating an interrupt lag time. The requested interrupt time period is then reduced based on the interrupt lag time.

In another illustrated embodiment, an antialiasing method for drawing a waveform on a display device is provided. The display device has an array of pixels, and the array includes a plurality of rows and columns. In accordance with the invention, background, foreground and intermediate pixel colors are selected. A plurality of interconnected wave line segments that form the waveform are determined, each wave line segment extending between first and second end pixels that are located in adjacent pixel columns. One-pixel wide waveform lines are drawn, in the foreground color, between the first and second end pixels of each wave segment, each waveform line having a midpoint wherein it switches columns from the column including its first end pixel to the column including its second end pixel. Additionally, an antialiasing line segment is drawn, in the intermediate color, for at least one waveform line. The antialiasing line segment has the same midpoint as and creates a mirror image of its corresponding waveform line.

In another illustrative embodiment, an antialiasing method is provided for controlling a graphics drawing package to draw a waveform on a display device. The display device has an array of pixels that includes a plurality of rows and columns. The graphics drawing package has a line drawing primitive which draws lines between two selected pixels. In accordance with the invention, foreground, background and intermediate pixel colors are selected. A plurality of interconnected wave line segments that form the waveform are determined, each wave line segment extending between first and second end pixels that are located in adjacent pixel columns. The first and second end pixels each have column and row coordinates indicating their position on the display device. Each wave line segment of the waveform is drawn by calling the line drawing primitive three times. The line drawing primitive is called to draw, in the intermediate color, a first line between the first end pixel of the wave line segment and a pixel having a column coordinate equal to the column coordinate of the first end pixel, and a row coordinate equal to the row coordinate of the second end pixel. The line drawing primitive is also called to draw, in the intermediate color, a second line between the second end pixel of the wave line segment and a pixel having a column coordinate equal to the column coordinate of the second end pixel, and a row coordinate equal to the row coordinate of the first end pixel. Finally, the line drawing primitive is called to draw, in the foreground color, a third line between the first and second end pixels of the wave line segment.

BRIEF DESCRIPTION OF THE DRAWINGS

FIGS. 8(a)–(d) are tables demonstrating the percentage of CPU usage for various methods of implementing antialiasing techniques using the X Window System;

FIG. 10 illustrates a waveform drawn using the antialiasing process of the present invention.

DETAILED DESCRIPTION OF PREFERRED EMBODIMENTS

Figure 3:
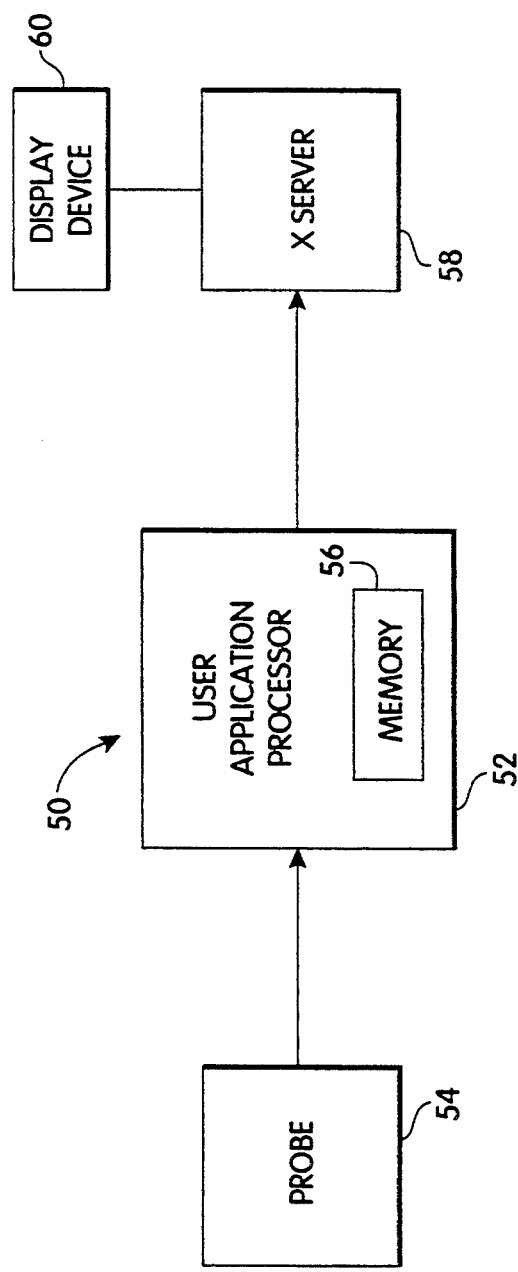
FIG. 3 illustrates one embodiment of the waveform updating and antialiasing system of the present invention.

As stated above, one embodiment of the present invention is directed toward a method and apparatus for drawing waveforms in a monitoring system utilizing a non-real time operating system such as UNIX, and an industry standard graphics package such as the X Window System. FIG. 3 illustrates an example of a hardware implementation of the waveform updating and antialiasing system of the present invention. The system 50 includes a processor 52 for performing a user application. As stated above, the present invention can be used in different types of applications to implement systems for monitoring different types of data sources, including various physiological conditions of a medical patient. Processor 52 includes a memory 56 and is coupled to a probe 54 that is used to receive an analog signal from a data source (not shown) and to sample the signal to convert the analog signal into a plurality of data samples. Processor 52 is also coupled to an X server 58 which is in turn coupled to a display device 60 which can be a CRT or other type of display. The display device is used to display a waveform representing the time-varying characteristics of a data source coupled to probe 54. The X server 58 is a dedicated processor, sometimes known as an X terminal, that includes software for implementing the X Window System graphics drawing package. Processor 52 can be a Hewlett Packard Apollo 9000 Series 700 Model 715/33 workstation, or any other type of suitable hardware system.

A software program for implementing the particular user application is performed on processor 52 and operates under an operating system that may be a non-real time operating system such as UNIX. Data samples collected from the data source are stored in memory 56 prior to their being used to update the waveform. The user application program requests periodic interrupts of the operating system for the purpose of updating the waveform. When the operating system services the interrupts, the user application program transfers selected data samples to the X server 58 for use in updating the waveform displayed on display device 60. X server 58, in a manner more fully described below, calculates which pixels are to be modified to update the waveform with each set of data samples that it receives.

Although the X server and the user application are illustrated in FIG. 3 as being implemented on separate processors, in another embodiment of the invention they are implemented on a single processor. In that embodiment, the X server and the user application are distinct software programs that are executed on the same processor.

For the purpose of explanation, the method and apparatus of the present invention will hereafter be described as being implemented on a monitoring system utilizing the non-real time UNIX operating system. However, it should be understood that the invention can be performed with any non-real time operating system, and that it can also be used to provide added flexibility to the scheduling of waveform updates in real-time monitoring systems. Additionally, although an ECG monitoring system is described for the purpose of illustration, the invention is not limited to this application and can be used to implement other monitoring systems.

Non-real time operating systems do not support frequent and consistent interrupts. Therefore, a monitoring system utilizing a non-real time operating system cannot schedule waveform updates in the lock-step manner of the above-described real-time systems because in non-real time systems, every interrupt will not necessarily be serviced promptly. For example, in prior art real-time monitoring systems for displaying a patient's ECG, regular interrupts are requested every 32 ms and must be serviced promptly within a small margin of error in the range of ±2 ms. By ensuring that the regular interrupts are serviced promptly, real-time operating systems allow the waveform to be updated in a lock-step manner whereby the waveform is updated with the same number of data samples following each interrupt, and whereby the waveform is essentially updated as the data samples are received.

The above-described lock-step updating of the waveform cannot be performed on a monitoring system that utilizes a non-real time operating system such as UNIX. UNIX does not support regular and precise interrupts due to context switch latencies, as well as the internals of the UNIX scheduler. Therefore, although regular interrupts can be requested, each will not necessarily be precisely serviced within a small margin of timing error. For example, if an ECG monitoring system were implemented utilizing UNIX, regular interrupts could be requested every 32 ms. However, UNIX cannot ensure that the interrupts will always be serviced precisely at 32 ms intervals and at times, interrupts might be serviced after delays of 64 ms or more. When the elapsed time period between the servicing of interrupts varies, the number of data samples received between the servicing of successive interrupts also necessarily varies. For example, if an interrupt requested to occur 32 ms after the previous waveform update is not serviced until 64 ms has elapsed, the number of data samples stored since the previous waveform update will be equal to twice the number that would have been stored if the interrupt were serviced promptly. If the waveform were updated only with the number of data samples that were expected to have been received within the requested 32 ms interrupt time period, the waveform displayed by the monitoring system would begin to lag behind the data source and the amount of lag would increase each time there was a delay in servicing an interrupt.

It is undesirable for the waveform displayed on a monitoring device to lag significantly behind the data source that it represents. For example, in a system for monitoring a patient's heartbeat, an attendant will monitor the patient by looking at the displayed waveform. If a problem occurs, it is desirable to have the problem indicated on the monitoring system as soon as possible so that the attendant can take appropriate action. Therefore, it is undesirable to allow the waveform to lag significantly behind the data source. The amount of waveform lag that may be tolerated varies depending upon the particular user application. With regard to ECG monitoring systems, no firm guidelines have been established because prior art monitoring systems operate on a real-time basis and do not lag behind the data source. However, some rough guidelines have been determined. For an ECG monitoring system located at the patient's bedside in an intensive care unit or in an operating room, it is believed that the waveform should not lag behind the input signal from the patient by more than ¼ second. However, for an ECG monitoring system located in a centralized location wherein display devices monitor multiple patients, it is believed that the requirement is less exacting and that a waveform that lags behind the input signal from the patient by a full second may be tolerated.

One way to ensure that the waveform displayed by the monitoring system will not lag significantly behind the data source is to update the waveform, whenever an interrupt is serviced, with all the stored data samples that have not yet been displayed. For example, in the ECG monitoring system wherein regular interrupts are requested every 32 ms, if various interrupts were not serviced until time periods of 64 ms, 96 ms or 128 ms had elapsed, the waveform could be respectively updated with two, three and four times the number of data samples that would have been updated if the 32 ms interrupt had been serviced promptly. In this manner, the waveform would not lag significantly behind the input signal from the patient because each time an interrupt was serviced, all of the data samples that had been received up to that point would be displayed.

When a large delay is experienced between the time that an interrupt is requested and serviced, it is not desirable to simply update the waveform with all the data samples received subsequent to the servicing of the previous interrupt. As described above, monitoring systems represent the data source with a fixed wave and it is desirable to ensure that the erase bar moves across the display screen at a constant velocity. However, when a non-real time operating system is used, a delay of two, three, four or more times the requested interrupt period may occur before the requested interrupt is serviced, resulting in two, three, four or more times the typical number of data samples being stored. If each time an interrupt were serviced the waveform were simply updated based on the total number of stored data samples, the system could not ensure that the erase bar would move across the display screen with a constant velocity. The erase bar might appear to slow down when a long delay is incurred prior to the servicing of a requested interrupt, and when the interrupt was serviced, the erase bar would rapidly jerk forward when the waveform was updated with the large number of data samples stored during the delay.

The present invention provides a method and apparatus for scheduling waveform updates on a monitoring system. The wave update scheduler ensures that the waveform does not unacceptably lag behind the data source, while simultaneously ensuring that the erase bar moves across the display screen with a substantially constant velocity. The waveform is maintained in close relationship with the data source in two ways. First, when a delay is incurred in the servicing of an interrupt, the wave update scheduler updates the waveform with more than the typical number of data samples that were expected to have been stored during the requested interrupt time period. In this manner, if there is a backlog of data samples to be updated to the display device, the wave update scheduler increases the number of data samples updated in order to reduce the backlog and to catch up with the data source. However, as is more fully described below, a limit is placed on the number of data samples that are updated during the servicing of any single interrupt to ensure that the erase bar moves across the display screen with a substantially constant velocity and does not rapidly jerk forward following a delay in the servicing of an interrupt. This aspect of the present invention can be considered as a coarse correction process because when the monitoring system lags behind the data source, this process allows it to catch up rather quickly.

The second way in which the wave update scheduler maintains the waveform in close relationship with the data source is through altering the time period for requested interrupts. When it is determined that the waveform is lagging behind the data source, the wave update scheduler shortens the time period to be expired before the next interrupt is requested. In this manner, when the monitoring system begins to fall behind the data source, interrupts are requested more frequently, thereby allowing more frequent updates of the stored data samples and enabling the monitoring system to catch up with the data source. This aspect of the present invention can be considered as a fine correction process because it operates to keep the monitoring system synchronized with the data source.

In one embodiment of the invention, the coarse and fine correction processes are performed simultaneously. However, it should be understood that the present invention can also be practiced by using either of these scheduling processes individually.

Figure 4:
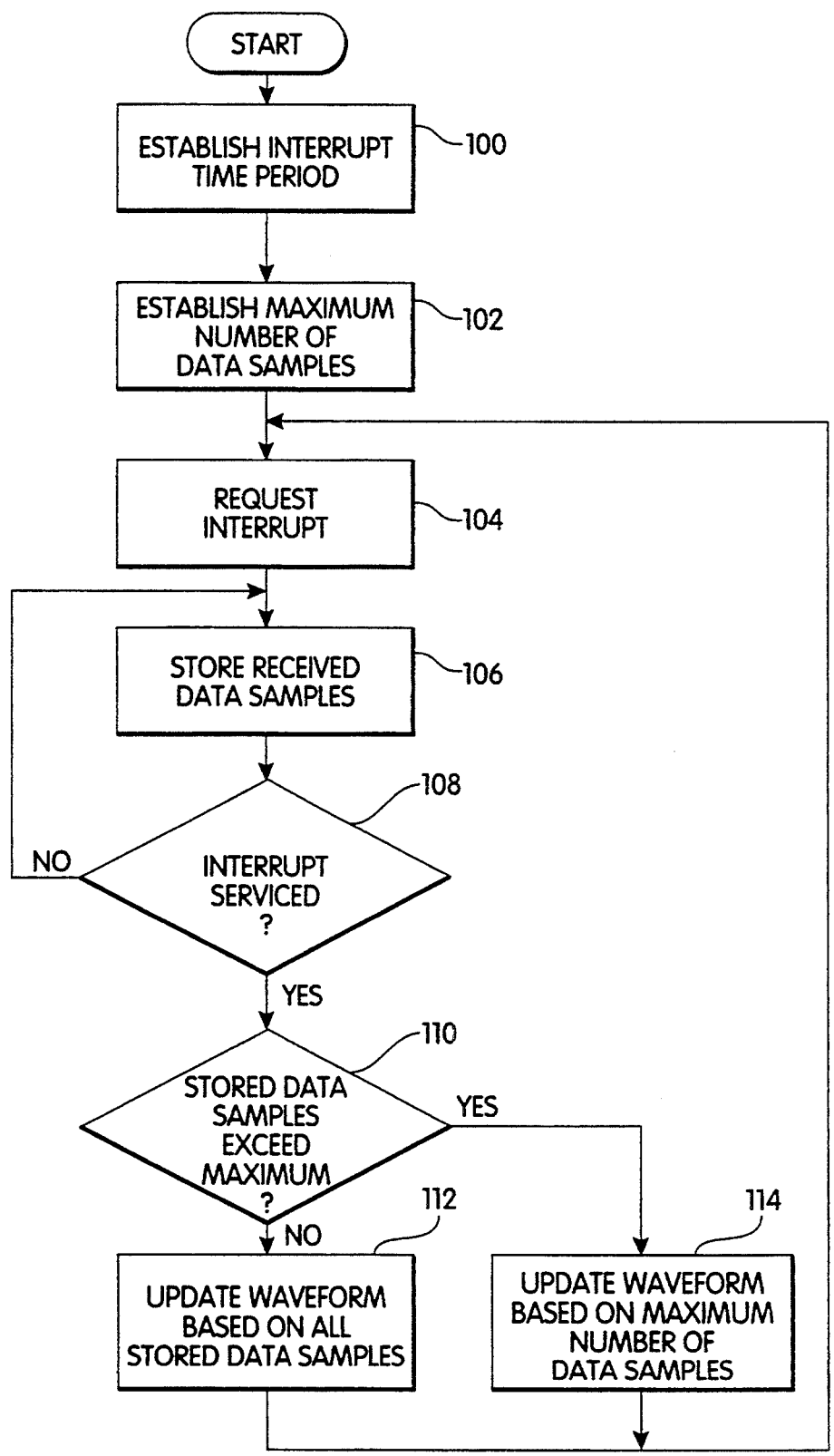
FIG. 4 is a flowchart of the steps of the coarse correction component of the wave scheduling process of the present invention.

FIG. 4 is a flowchart of the coarse correction process of the present invention. The process illustrated in FIG. 4 is implemented by a software routine that is executed on the user application processor 52 (FIG. 3).

At step 100, an interrupt time period is established. The interrupt time period establishes the amount of time that will elapse between the requesting of interrupts to the operating system. The interrupt time period is predetermined based upon the particular user application and is selected so that if every interrupt were promptly serviced at the expiration of the interrupt time period, the updating of the waveform would be synchronized with the data samples received from the data source.

At step 102, a maximum number of data samples to be updated in response to the servicing of any single interrupt is established. The maximum number is also predetermined based upon the particular user application. As described above, when a long delay is experienced between the requesting and servicing of an interrupt, a large number of data samples will be received from the data source and stored. If each of the stored data samples was used to update the waveform when the interrupt was serviced, the erase bar would jerk forward and would not maintain the desired constant velocity. Therefore, although it is desirable to update the waveform with as many data samples as possible so that the monitoring system will not lag behind the data source, a limit is imposed to ensure that the erase bar maintains a constant velocity. The maximum rate is established for each user application to control the maximum number of data samples that may be updated at the servicing of any single interrupt to ensure that the erase bar maintains a substantially constant velocity.

At step 104, the next interrupt is requested at the expiration of the interrupt time period determined at step 100. Thereafter, the data samples received from the data source are stored at step 106. At step 108, a determination is made as to whether the requested interrupt has been serviced and when it has not, the process returns to step 106 to continue to store the received data samples. In this manner, the process continues to store received data samples and wait until it is determined at step 108 that the interrupt has been serviced.

When it is determined at step 108 that the interrupt has been serviced, the process proceeds to step 110 wherein a determination is made as to whether the number of stored data samples exceeds the maximum number established at step 102. When it is determined at step 110 that the number of stored data samples does not exceed the maximum number, the waveform can be updated based upon all of the stored data samples without having the erase bar appear excessively jerky. Therefore, the method proceeds to step 112 wherein the waveform is updated based upon all the stored data samples. As with the prior art monitoring systems described above, a decimation algorithm is performed on the stored data samples to select a representative subset of data samples for the purpose of display. Although each stored data sample is not selected by the decimation algorithm to actually be displayed, the waveform is nevertheless updated based upon all of the stored data samples because each of these data samples is input to the decimation algorithm and the data samples selected for display are representative of all the stored data samples. Therefore, the statement that the waveform is updated based upon all the data samples is used herein to indicate that the data samples actually displayed when the waveform is updated are representative of all the stored data samples.

When it is determined at step 110 that the number of stored data samples exceeds the maximum number, the process proceeds to step 114 wherein the waveform is updated based on only the maximum number of data samples. In this step, the waveform is not updated based on all of the stored data samples. The data samples that are not used for the purpose of updating the waveform are stored and used to update the waveform at the servicing of subsequent interrupts. In this manner, the process limits the number of data samples that is used to update the waveform at the servicing of any single interrupt, thereby ensuring that the erase bar maintains a substantially constant velocity.

After the waveform has been updated at either of steps 112 or 114, the process returns to step 104 wherein the next interrupt is requested. In this manner, the process continues to request interrupts of the operating system in order to update the waveform with data samples received from the data source.

Figure 5:
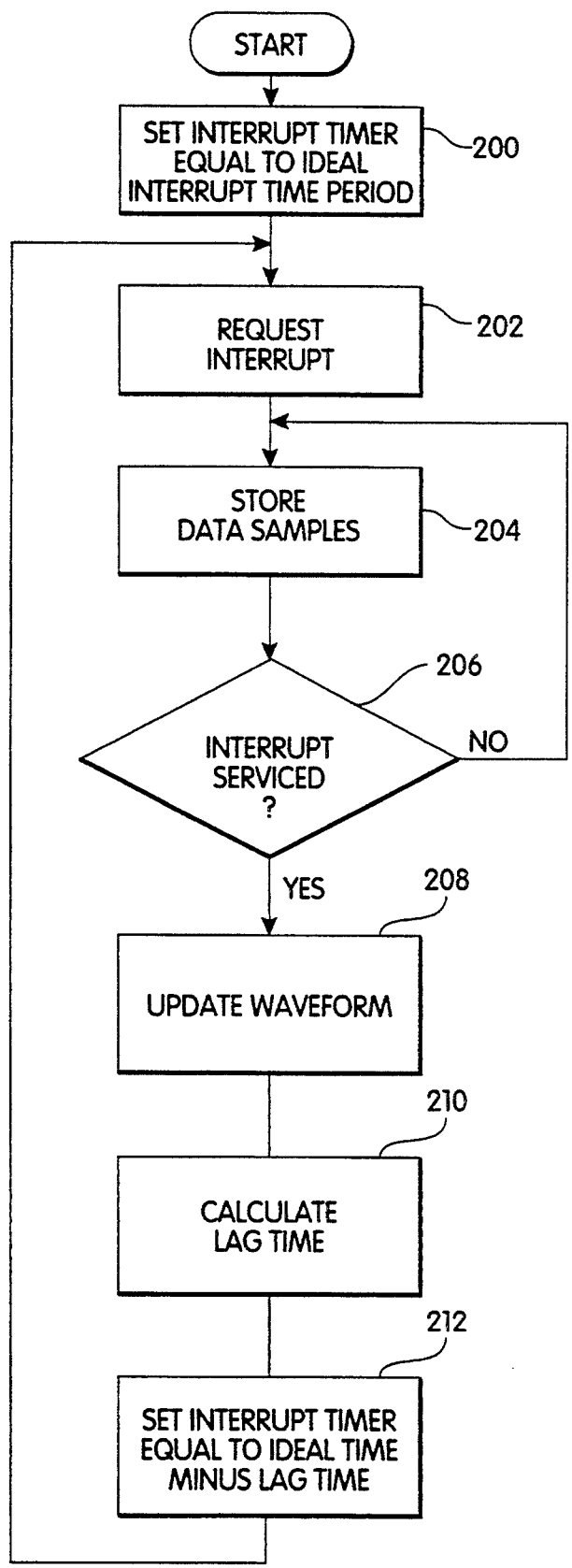
FIG. 5 is a flowchart of the steps of the fine correction component of the wave scheduling process of the present invention.

FIG. 5 is a flowchart of the fine correction process of the present invention. The process is also implemented by a software routine that is executed on the user application processor 52 (FIG. 3). At step 200, an interrupt timer is set equal to an ideal interrupt time period. The ideal interrupt time period is predetermined, based upon the particular user application, so that if every interrupt were promptly serviced at the expiration of the ideal interrupt time period, the updating of the waveform would be synchronized with the data samples received from the data source.

At step 202, an interrupt is requested to occur when the interrupt timer expires. Thereafter, the data samples received from the data source are stored at step 204. At step 206, a determination is made as to whether the requested interrupt has been serviced and when it has not, the method returns to step 204. In this manner, the process continues to store the data samples received from the data source and wait until it is determined that the interrupt has been serviced.

When it is determined at step 206 that the interrupt has been serviced, the process proceeds to step 208 wherein the waveform is updated based upon at least some of the data samples that have been received from the data source.

At step 210, a lag time is calculated. The lag time indicates a time difference between the time when the interrupt was requested to be serviced, and the time when it was actually serviced. Thus, the lag time indicates the amount by which the servicing of the interrupt lags behind the time at which it was requested.

At step 212, the interrupt timer is set equal to the ideal interrupt time period minus the lag time. In this manner, when the monitoring system lags behind the data source, the method requests that the next interrupt be serviced more quickly. This feature of the fine correction process of the present invention is designed to prevent the monitoring system from slowly and increasingly lagging behind the data source. After the interrupt timer has been set at step 212, the process returns to step 202 wherein the next interrupt is requested to be serviced after the interrupt timer expires. In this manner, the process continually requests interrupts of the operating system so that the waveform can be updated.

The processes shown in FIGS. 4 and 5 can each be performed independently for the purpose of scheduling waveform updates on monitoring system using a non-real time operating system. Each of these processes can be implemented through a variety of methods. Additionally, the coarse and fine correction processes of the present invention can also be performed together and can be implemented by a single method.

Figure 6:
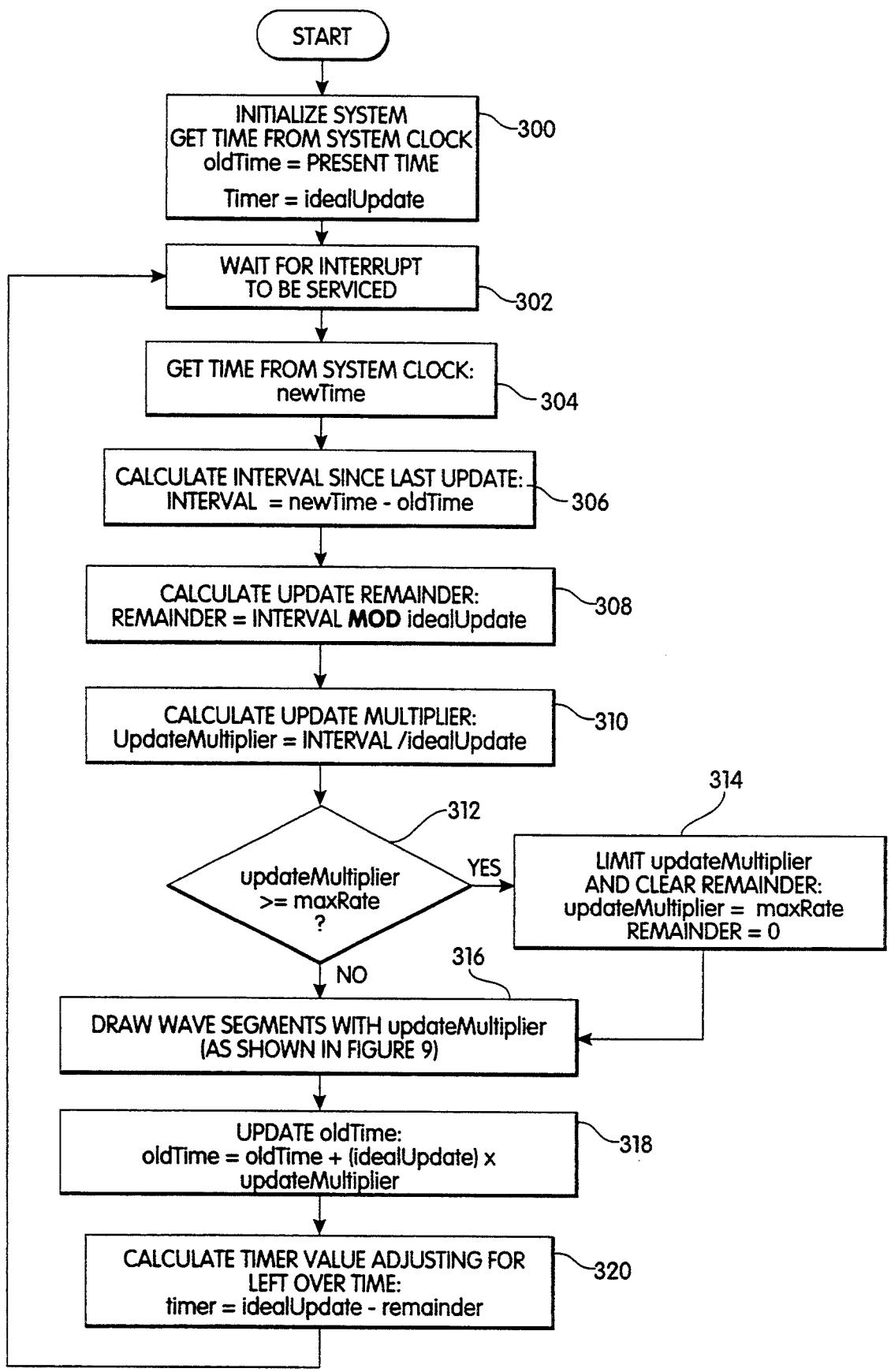
FIG. 6 is a flowchart of the steps of one method for implementing the waveform updating process of the present invention.

Reference is now made to FIG. 6 which is a flow chart of one particular method for implementing the wave update scheduling process of the present invention. This particular method has been found to implement the wave update scheduling process in an accurate and efficient manner, and implements both the coarse and fine correction processes described above. However, it should be understood that this method is provided for illustrative purposes only and that the invention is not limited to this particular method. Alternate methods can also be utilized to implement the wave update scheduling process of the present invention based upon the teachings provided herein.

The method illustrated in FIG. 6 is implemented by a software routine that is executed on the user application processor 52 (FIG. 3). At step 300, the method is initialized in two ways. First, a timer labeled "oldTime" is set equal to the initialization time indicated by the system clock. Second, a variable labeled "timer" is initialized. The timer establishes the time at which the next interrupt will be requested. When the wave update scheduling process is performed on a system utilizing UNIX, the timer is implemented using the UNIX "select" function. UNIX "select" is typically used to wait for and receive input information from a file with an optional timeout on failure. If no file is specified in calling the "select" function, the function becomes a fine granularity timer. The "select" function is used rather than the UNIX timer because it is more precise and has a finer granularity. The timer is initialized at step 300 by setting it equal to a constant labeled "idealUpdate". IdealUpdate is a time period individually established for each user application and indicates the ideal time period that should expire between the servicing of consecutive interrupts. The ideal update time period is preferably set equal to a whole number multiple of the frequency at which data samples are received from the data source, the whole number indicating the number of data samples upon which the updating of the waveform will ideally be based at the servicing of each interrupt. In this manner, if each interrupt is serviced promptly, the monitoring system will be synchronized with the data source. For example, when the wave update scheduling process is used to implement a system for displaying an ECG, idealUpdate will generally be established as being 32 ms, and the waveform would ideally be updated based upon sixteen data samples at the servicing of each interrupt.

After initialization, the method proceeds to step 302 wherein it waits for the idealUpdate time period to expire and for the requested interrupt to be serviced. Once the interrupt is serviced, the method proceeds to step 304 wherein a variable labeled "newTime" is set equal to the system clock so as to indicate the time at which the interrupt was serviced.

At step 306, a variable labeled as "interval" is set equal to newTime minus oldTime. Thus, interval indicates the amount of time that has elapsed between the servicing of the most recent interrupt, and the initialization of the method. As will be seen from the description provided below, certain steps in the method of FIG. 6 are iteratively performed and near the end of each iteration, oldTime is updated to indicate the time at which the interrupt occurred. Therefore, during later iterations of the method, interval indicates the amount of time expired between the previous interrupt and the interrupt being serviced.

After the interrupt time interval has been calculated, the method proceeds to steps 308 and 310 wherein the actual interrupt time interval is divided by the ideal update time period. As a result of the division, a variable labeled as "updateMultiplier" is set equal to the quotient at step 310, and a variable labeled as "remainder" is set equal to the remainder at step 308. For example, if the ideal update time period is established as being equal to 32 ms and the interrupt is serviced at 35 ms, then when the interrupt interval (35 ms) is divided by the ideal update time period (32 ms), updateMultiplier is set equal to one and the remainder is set equal to 3 ms. Similarly, if the interrupt interval indicating the time period elapsed prior to servicing the interrupt is equal to 67 ms, then updateMultiplier is set equal to two and the remainder is set equal to 3 ms. Thus, after steps 308 and 310 are performed, updateMultiplier is a whole number indicating the number of times that the ideal update time period is divisible into the actual elapsed time interval between the servicing of successive interrupts, and the remainder is equal to the remaining time period.

At step 312, a determination is made as to whether updateMultiplier exceeds a predetermined maximum rate. The maximum rate is established, based upon the particular user application, to limit the number of data samples that can be updated in response to the servicing of any single interrupt. As described above, when a long period of time elapses between the servicing of successive interrupts, a large number of data samples is stored. This condition is indicated by the variable "interval" being large in comparison to the ideal update time period. If a large number of data samples was updated when the interrupt was serviced, the erase bar would jerk forward and would not maintain the desired constant velocity. The maximum rate is established for each user application to control the maximum number of data samples that may be updated at the servicing of any single interrupt to ensure that the erase bar maintains a substantially constant velocity. For the ECG application described above, it has been found that a satisfactory maximum rate is twice the typical number of data samples updated when an interrupt is serviced promptly at 32 ms. A maximum rate of twice the number of data samples ideally updated has been found to allow the system to quickly catch up after it falls behind the data source, and although the erase bar moves forward more quickly when updated with twice the typical number of data samples, it has been found that the velocity of the erase bar is sufficiently constant and does not appear excessively jerky. Another guideline for determining the maximum number of data samples to be updated at the servicing of a single interrupt is the ability of the user to detect changes in the velocity of the erase bar. As long as the erase bar is not updated at less than the rate of sixteen times per second, the user will not be able to perceive the writing of individual line segments because sixteen updates per second is the minimum animation rate at which the human eye perceives discrete updates as continuous motion. The minimum number of data samples that should be presented corresponds to the amount of data received from the data source in 64 ms (i.e., 1/16th of second). For an ECG monitoring system sampled every 2 ms, this minimum number of data samples is thirty-two.

When it is determined at step 312 that updateMultiplier exceeds the maximum rate, the method proceeds to step 314 wherein updateMultiplier is set equal to the maximum rate, and the remainder is set equal to zero. UpdateMultiplier is set equal to the maximum rate to ensure that fewer than the total number of stored data samples will be updated. As is described more fully below, the method determines how many data samples to update by multiplying updateMultiplier by a constant representing the number of data samples that would ideally be updated if the interrupt were serviced precisely when requested. If updateMultiplier exceeds the maximum rate, updateMultipler must be reduced prior to performing the wave drawing steps described below, or too many data samples would be updated, thereby causing the erase bar to jerk forward. By setting updateMultiplier equal to the maximum rate at step 314, the method ensures that when the waveform segments are drawn, only the maximum number of data samples will be updated. For example, if the ideal update period was established as being 32 ms and an interrupt was not serviced until 128 ms elapsed, updateMultiplier would be set equal to four at step 310. If the maximum rate were established as being equal to twice the number of data samples ideally updated, the method would, at step 314, reduce updateMultiplier to two in order to limit the number of data samples that would be updated. Thus, when the waveform segments were drawn in the manner described below, the number of data samples updated would be limited to the maximum acceptable number.

Setting the remainder equal to zero at step 314 is also done to ensure that the erase bar maintains a substantially constant velocity. Step 314 is only performed when the waveform will be updated with the maximum number of data samples. Therefore, by setting the remainder equal to zero, the method ensures that the next interrupt will not be requested to occur early. If the next interrupt were to occur too soon after the waveform had been updated with the maximum number of data samples, the erase bar might appear to jerk forward too rapidly.

When it is determined at step 312 that updateMultiplier does not exceed the maximum rate, each of the stored data samples can be updated without having the erase bar appear excessively jerky. Therefore, updateMultiplier need not be limited, and the method proceeds directly to step 316.

At step 316, the waveform is updated utilizing updateMultiplier to determine how many data samples the waveform update will be based upon. The manner in which the waveform is updated is described more fully below.

After the waveform is updated, the method proceeds to step 318 wherein the variable oldTime is updated by adding to its value the product of updateMultiplier and the ideal update time period. OldTime is updated in this manner because it is used to track which of the stored data samples have been updated. As described above, the method limits the number of data samples that can be updated when any single interrupt is serviced. Therefore, when the number of stored data samples exceeds the maximum update rate, fewer than the total number of stored data samples will be updated. The method utilizes oldTime to keep track of which of the stored data samples have been updated, and which need to be updated when subsequent interrupts are serviced.

After oldTime is updated, the method proceeds to step 320 wherein the "timer" variable is set equal to the ideal update time period minus the remainder calculated at step 308. As a result, when the remainder has a non-zero value, "timer" will be set equal to less than the ideal update time period. By setting the interrupt request timer equal to less than the ideal update time period, the method requests that the next interrupt be serviced more quickly than the predetermined ideal update time period. In this manner, when the monitoring system lags behind the data source by a slight amount, the method requests that the next interrupt be serviced more quickly. This feature of the wave update scheduling process is designed to prevent the monitoring system from increasingly lagging behind the data source. For example, if the ideal update time period is 32 ms and the interrupt is serviced after 35 ms, the remainder will be set equal to 3 ms at step 308. When the update wave scheduling process reaches step 320, the timer will be set equal to 29 ms. In this manner, the monitoring system will tend to make up the 3 ms that it had previously fallen behind because the next interrupt is requested at a quicker rate than that at which the data samples are provided from the data source. As described above, the remainder of the division performed at steps 308 and 310 is used to determine the amount by which the servicing of the interrupt lags behind the requested interrupt time. However, it should be understood that the lag time could be determined in other ways, such as by subtracting the time at which the interrupt was requested to be serviced from the actual time at which it was serviced.

After the "timer" variable is updated at step 320, the method returns to step 302 wherein it waits for the next time out. In this manner, the method continually establishes an interrupt timer for requesting interrupts of the operating system, and when the interrupts are serviced, causes the waveform displayed on the display device to be updated. As described above, the method ensures that the monitoring system does not lag substantially behind the data source and when it begins to lag behind, the method takes steps to catch up with the data source. In this regard, it can be seen from the method shown in FIG. 6 that when the monitoring system begins to lag behind the data source, the update wave scheduling process utilizes both coarse and fine correction factors to cause the monitoring system to catch up. When the monitoring system has fallen behind and has a large number of data samples to update, the wave update scheduling process increases the number of data samples that are updated when an interrupt is serviced. This action can be considered as a coarse correction factor which causes the wave update scheduling process to catch up to the data source relatively quickly. Additionally, when the monitoring system begins to lag slightly behind because interrupts are serviced slightly later than requested, the interrupt timer is adjusted to request subsequent interrupts more quickly. This step can be considered as a fine correction factor which tends to keep the monitoring system in line with the data source and prevents it from falling further and further behind.

As stated above, the method illustrated in FIG. 6 is provided merely for illustrative purposes and it will be understood that the wave update scheduling process of the present invention can be implemented in a number of other ways. For example, in the method described above, the number of data samples updated at the servicing of any interrupt is equal to the ideal number of data samples to be updated multiplied by a whole number (updateMultiplier). In one embodiment of the invention, the number of data samples updated is always limited to a whole number multiple of the number of data samples that would ideally be updated if all interrupts were serviced promptly because it provides for ease in interfacing the wave update scheduling process of the present invention with existing decimation algorithms used with prior art real-time monitoring systems. As described above, decimation algorithms are used to reduce, in an intelligent fashion, the number of data samples received from a data source into a subset of representative data samples for display on the display device. Since real-time monitoring systems work in a lock-step fashion, the decimation algorithms developed for those systems receive a constant number of data sample inputs and convert them to a constant number of representative data sample outputs for display. By limiting the number of data samples updated to a whole number multiple of the number of data samples ideally updated, the method of FIG. 6 can easily interface with decimation algorithms used with prior art real-time monitoring systems. For each interrupt serviced, the data samples to be updated can be divided into one or more sets of data samples wherein each set includes the same number of data samples updated in the real-time systems. Each set of data samples can be updated separately so that the existing decimation algorithms can operate separately on each set. For example, if updateMultiplier equals two, the update wave scheduling process of the present invention can simply call an existing decimation algorithm twice, once to operate upon each set of data samples. Since the number of data samples to be updated in each set equals the number that is always updated in the real-time monitoring systems, those same decimation algorithms can be used with the method shown in FIG. 6.

Although the embodiment of the invention shown in FIG. 6 limits the number of data samples that can be updated at the servicing of a single interrupt to a whole number multiple of the number of data samples ideally updated, the invention is not so limited. Existing decimation algorithms can be modified to receive and output variable numbers of data samples. When modified decimation algorithms are used, the wave update scheduling process of the present invention is not constrained to update only whole number multiples of the ideal number of data samples, and could update any number of data samples that is less than the maximum number established for the user application.

Figure 2:
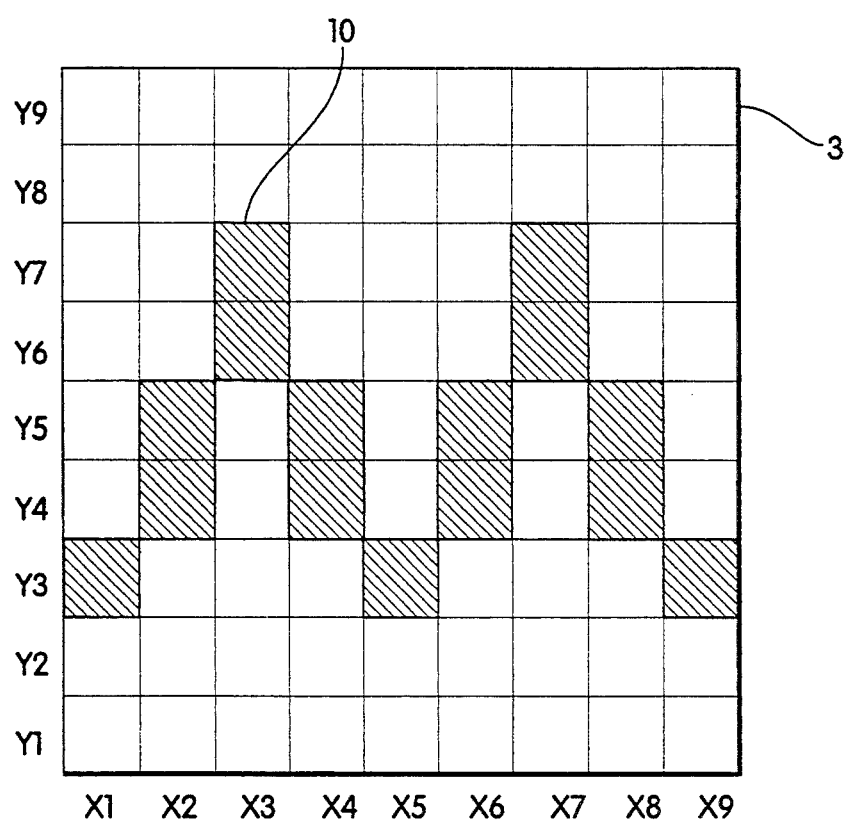
FIG. 2 illustrates a waveform drawn without the use of antialiasing techniques.

As stated above, when waveforms are drawn on a display screen, an undesirable effect known as aliasing may occur wherein the waveform, as shown for example in FIG. 2, has a stair-step, or jagged, appearance. As further stated above, antialiasing techniques have been developed to reduce the jagged appearance of waveforms by using a color intermediate to the foreground and background colors to soften the transition edges of the waveform. Because monitoring systems have typically been implemented using proprietary hardware and software, the foreground, background and intermediate colors have typically been predetermined by system hardware or fixed code so that the colors are not easily adjustable and the user has a limited number of selections. Historically, the background color is black and the waveform is drawn in a green foreground color, although more recently developed proprietary systems make use of other foreground and background colors.

As stated above, the present invention provides a method and apparatus for implementing antialiasing techniques that are compatible with a standard graphics drawing package, such as the X Window System. Standard graphics drawing packages enable a user to dynamically select the foreground and background colors without significant restriction, except that the foreground and background colors must obviously be different. The foreground color may have less intensity than the background color such that a dark waveform may be displayed on a light background.

In order to implement antialiasing techniques with a standard graphics drawing package, an intermediate color must be selected for the particular foreground and background colors chosen. The most important factor in choosing the intermediate color is to select a color that is most effective in smoothing the jagged appearance of the waveform. This can be accomplished through human factors testing whereby individuals can view waveforms drawn with antialiasing techniques using a multitude of intermediate colors and can select the intermediate color that produces the smoothest looking waveform. The intermediate color should be intermediate to the foreground and background colors with respect to each of hue, intensity and saturation. Experimental results have indicated that when a light waveform is drawn on a dark background and displayed on a cathode ray tube (CRT), an effective intermediate color is one that is linearly halfway between the foreground and background colors with regard to each of its red, green and blue components. When different types of display devices are used, or when a dark waveform is displayed on a light background, other criteria may be useful for selecting the intermediate color.

Once the foreground, background and intermediate colors have been selected, they are bound to a "graphics context" when the X Windows System is used, or to a similar function when another standard graphics drawing package is used. A graphics context is a set of information that interfaces a standard graphics drawing package to a user application and defines certain characteristics that will be used in the drawing of points or lines by the graphics drawing package. Examples of drawing characteristics that can be preselected and bound to a graphics context include the color of points or lines to be drawn with a selected context, as well as the width of any line drawn with the context. Once the selected foreground, background and intermediate colors are bound to respective graphics contexts, the user application selects the desired color by indicating its corresponding context.

As stated above, prior art monitoring systems were implemented with proprietary hardware and software. Therefore, these systems implemented antialiasing techniques that were customized for the wave drawing functions that they performed. Standard graphics drawing packages such as the X Window System are designed for general purpose use and can implement various graphics applications. Standard graphics packages typically support a number of drawing command primitives that allow the user application to perform various graphics functions. For example, standard graphics drawing packages typically enable the user application to issue commands that respectively draw points (single pixels), and to draw lines of different widths between two endpoints on the display device. The present invention provides a method and apparatus for implementing antialiasing techniques utilizing primitives provided by a standard graphics drawing package such as the X Window System.

FIG. 2 illustrates a waveform 10 drawn on a display device 3. The display device 3 is comprised of a plurality of pixels that are arranged in a two-dimensional array having coordinates that are labeled as X and Y in FIG. 2. The waveform 10 can be divided into a plurality of interconnected line segments wherein each line segment extends between two endpoints that are located in adjacent X columns so that each line segment has a delta-X of one. Thus, the waveform 10 can be broken down into eight waveline segments ws1–ws8 that respectively have the following pixels as endpoints:

ws1(x1,y3-x2,y4); ws2(x2,y4-x3,y7);
ws3(x3,y7-x4,y4); ws4(x4,y4-x5,y3);
ws5(x5,y3-x6,y4); ws6(x6,y4-x7,y7);
ws7(x7,y7-x8,y4); ws8(x8,y4-x9,y3).

Since any waveform can be divided into a plurality of wave line segments as described above, the line drawing primitive of a standard graphics drawing package can be used to draw a waveform by calling the line drawing primitive a plurality of times, one call to draw each wave line segment. In order to draw a wave line segment, the user application need only supply the standard graphics drawing package with a command indicating that a line is to be drawn, the XY coordinates of the pixels that define the endpoints of the line segment, and the graphics context (or similar function) to indicate the color and width of the line to be drawn.

Figure 7:
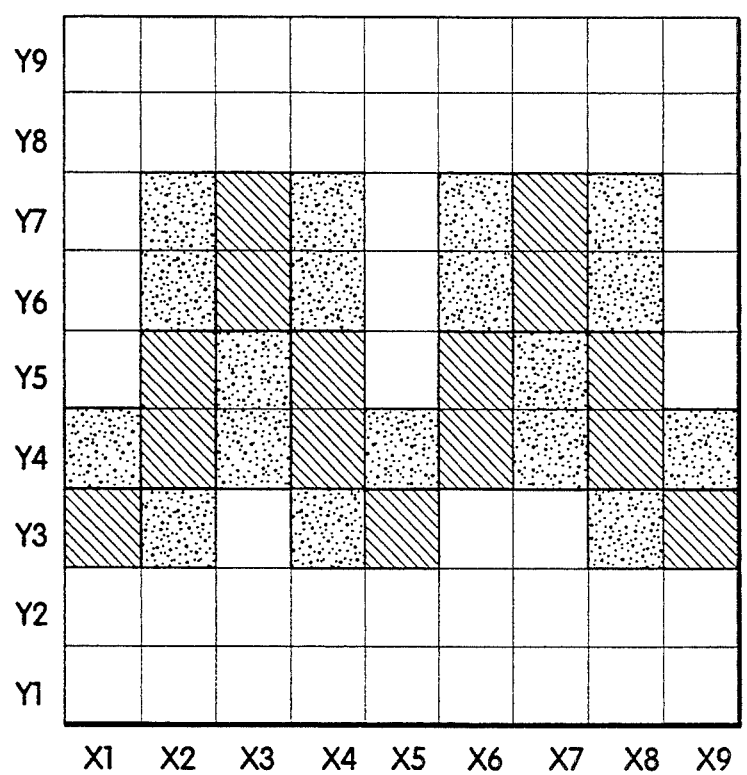
FIG. 7 Illustrates the waveform of FIG. 2 drawn using the antialiasing process of the present invention.

Through experimentation, it has been determined that an effective antialiasing technique can be implemented using a technique that is shown in FIG. 7. FIG. 7 illustrates the waveform of FIG. 2 drawn with this antialiasing technique wherein single and double cross-hatching respectively represent pixels drawn in the intermediate and foreground colors. As stated above, each line segment has a delta-X of one and therefore has a midpoint wherein the line segment switches from the column of pixels that includes its beginning point, to the column that includes its end point. The antialiasing technique shown in FIG. 7 uses antialiasing pixels, drawn in the intermediate color, for each line segment. Each line segment pixel drawn in the foreground color has a corresponding antialiasing pixel that is located in the same pixel row. The antialiasing pixels corresponding to line segment pixels located between the beginning and midpoint of the line segment are located in the pixel column that includes the line segment endpoint. Conversely, the antialiasing pixels corresponding to line segment pixels located between the midpoint and endpoint of the line segment are located in the pixel column that includes the beginning point. As a result, the antialiasing pixels for each line segment are positioned adjacent the wave line segment, switch columns at the line segment midpoint, and essentially produce a mirror image of the line segment.

There are a number of ways in which the antialiasing technique shown in FIG. 7 can be implemented. The X Window System provides a feature wherein lines can be drawn that are more than a single pixel in width. Utilizing this feature of the X Window System, the antialiasing technique illustrated in FIG. 7 can be implemented by drawing each waveform line segment twice. Initially, a two-pixel wide line is drawn in the intermediate color between the endpoints of the line segment. Thereafter, a one-pixel wide line is drawn between the endpoints in the foreground color. In this manner, the antialiasing technique shown in FIG. 7 is implemented with very simple code on the user application side in that only two X calls are needed per wave segment, one X call each for the foreground and intermediate color lines. However, this technique uses a great deal of the X server's CPU resources as can be seen from FIG. 8.

FIGS. 8(a)–(d) illustrate the percentage of CPU utilization when a Hewlett Packard Series 900 Model 425 workstation is used to implement both the X server and a user application consisting of an ECG monitor. Since the monitoring system can be used to simultaneously display waveforms from several different data sources, the tables provided in FIGS. 8(a)–(d) each show the percentage of CPU utilization for the rendering of seven, twelve and sixteen waves. FIG. 8(a) represents the percentage of CPU utilization when the waveform is drawn utilizing the X Window System line drawing primitive to draw each of the wave line segments in the manner described above, and when no antialiasing line segments are drawn.

FIG. 8(b) shows the percentage of CPU utilization when the antialiasing technique shown in FIG. 7 is implemented by using the X Window System feature enabling the drawing of two-pixel wide line segments in the intermediate color between the endpoints of each line segment. As can be seen from FIG. 8(b), a large percentage of the CPU is used by the X server when antialiasing is performed in this manner. This percentage of utilization of the CPU is undesirable because, particularly when a large number of waveforms are displayed simultaneously, there is little CPU power remaining to perform any other meaningful task. Therefore, other methods of implementing the antialiasing technique shown in FIG. 7 have been developed.

From an examination of X server benchmarks, it has been determined that the fastest operation performed by the X Window System on the above-described X server implementation is the drawing of a plurality of single pixel points, rather than the drawing of a line that includes the same pixels. Based upon this understanding, the antialiasing technique shown in FIG. 7 can be implemented by transferring to the user application the computations relating to which pixels should be illuminated to draw the desired line segments, and by using the X server to simply draw the determined points. A known technique for drawing a line is Bresenham's algorithm which uses only integer arithmetic and is therefore very fast. Bresenham's algorithm is described in the following publication: Bresenham, J. E. 1965 "Algorithm For Computer Control of Digital Plotter" IBM Systems Journal 4:25–30. As stated above, the waveform can be broken up into a plurality of wave line segments that each have a delta-X of one. By implementing Bresenham's algorithm, the user application can determine the midpoint location of each line segment where there is a shift in the column, and can determine which pixels should be drawn in the foreground color. Since each line segment has a delta-X of one, the antialiasing technique shown in FIG. 7 can be implemented by drawing intermediate color pixels between the line segment midpoint and the line segment endpoints so that they mirror the wave line segment. As the pixels are determined by the user application, they are stored in arrays. Each of the intermediate color pixels is then sent to the X server in a first bundle to be drawn as points, and each of the foreground color pixels is sent in a second bundle. In this manner, only two X calls are required per wave segment.

FIG. 8(c) shows the percentage utilization of the CPU attributable to the X server and the user application when the above-described Bresenham-based antialiasing technique is implemented. As can be seen from a comparison of FIGS. 8(b) and 8(c), a significant savings is achieved in the percentage utilization of the CPU by the X server when the antialiasing technique is implemented in this manner. However, when this method is used, complexity is added to the user application side of the system in that the determination of which pixels are to be drawn in each of the foreground and intermediate colors to render the waveform is made by the user application, rather than by the X server. This shift in processing is illustrated in FIG. 8(c) which demonstrates a significant increase in CPU utilization attributable to the user application as compared with FIG. 8(b).

In another embodiment of the invention, the antialiasing technique shown in FIG. 7 is implemented by drawing three one-pixel wide lines for each wave line segment. As stated above, the antialiasing technique shown in FIG. 7 can be achieved by using two X Windows line drawing commands for each line segment of the waveform, one line segment being two-pixels wide and in the intermediate color, and the second line segment being one-pixel wide in the foreground color. As was further described above, the X server does not efficiently draw line segments that are two-pixels wide. Therefore, in another embodiment of the invention, two one-pixel wide lines are drawn in the intermediate color rather than drawing a single two-pixel wide line. These antialiasing lines are drawn first, and then a one-pixel wide line is drawn in the foreground color. It has been found through experimentation that the X server is more efficient in drawing two one-pixel wide lines than it is in drawing a single two-pixel wide line.

FIG. 8(d) shows the percentage of CPU utilization attributable to the X server and the user application for this embodiment of the invention. As can be seen from a comparison of FIGS. 8(b) and 8(d), drawing two one-pixel wide lines rather than a single two-pixel wide line results in significant reduction in utilization of the CPU by the X server. Furthermore, although three X Windows line drawing commands must be issued by the user application rather than two, the increase in CPU utilization attributable to the user application is not particularly significant. Furthermore, as can be seen from a comparison of FIGS. 8(c) and 8(d), the percentage of user application CPU utilization for this embodiment is far less than the above-described Bresenham-based embodiment.

Figure 1A:
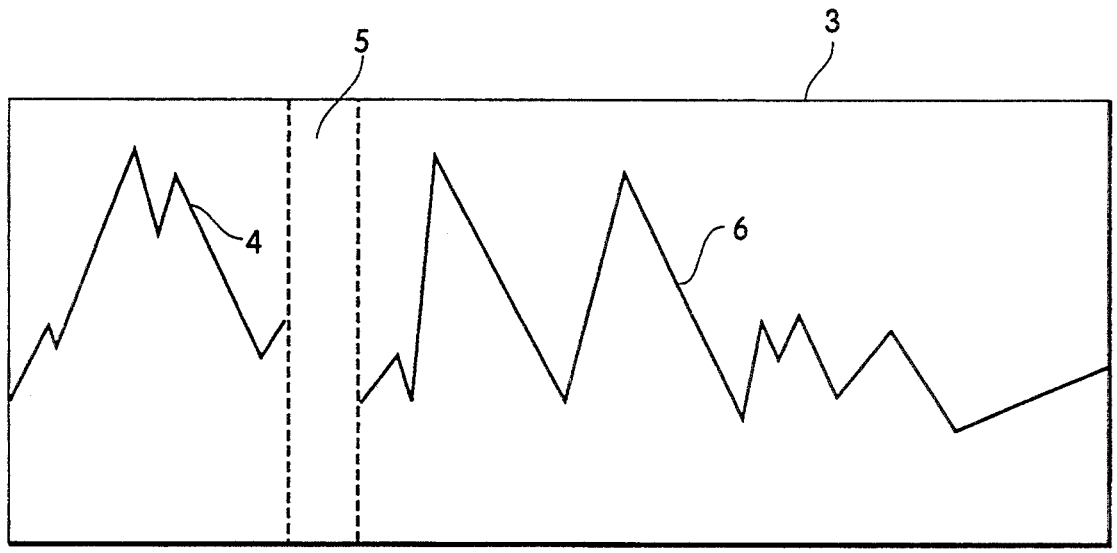
FIGS. 1(a)–(b) illustrate the movement of an erase bar across a displayed fixed waveform.
Figure 1B:
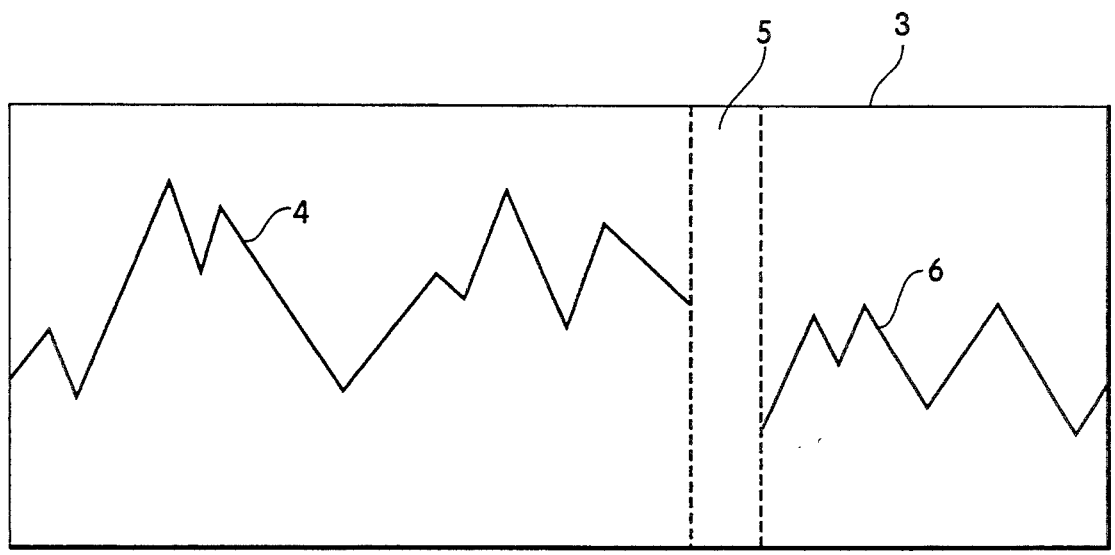
Figure 9:
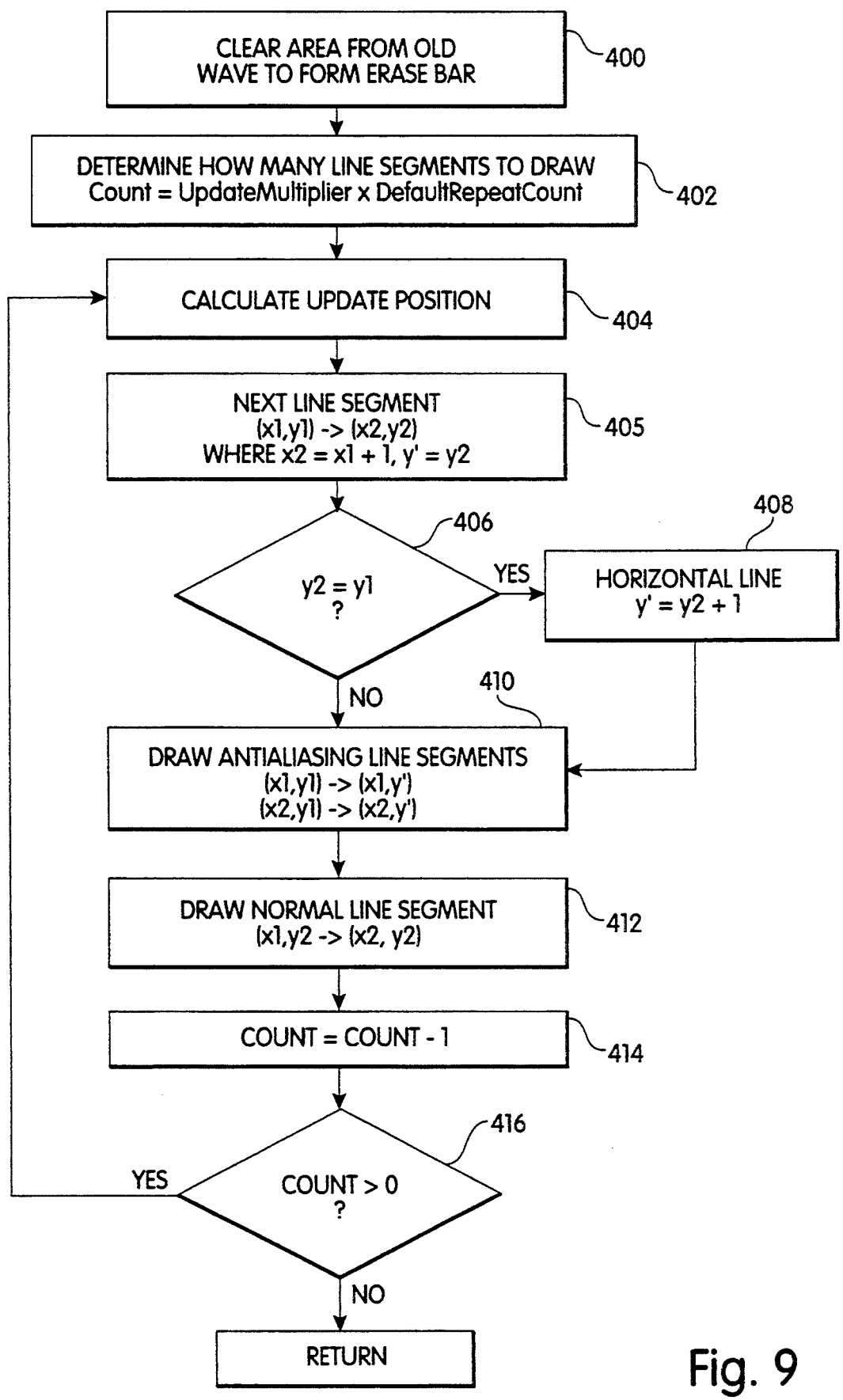
FIG. 9 is a flowchart of the steps of one method for implementing the antialiasing process of the present invention.

FIG. 9 is a flowchart of a method for implementing the antialiasing technique shown in FIG. 7 by using the above-described embodiment of the present invention wherein three X Windows line drawing commands are used for each waveform line segment. FIG. 10 illustrates a waveform drawn using the method shown in FIG. 9; the display background is black, the foreground color is white, and the intermediate color is represented by cross-hatching. The method shown in FIG. 9 is called by step 316 of the method shown in FIG. 6 wherein that step requests that wave segments be drawn for various data samples. Initially, at step 400 the area of the display screen on which the old waveform was displayed is cleared to form the erase bar. As was described above, the waveforms on the display device are fixed waves that wrap around and include an erase bar 5 (FIG. 1) that moves across the screen to indicate the updating of the waveform. At step 400, the old waveform is cleared from the screen by issuing a command to the X server to redraw each of the pixels in the erase bar area in the background color.

At step 402, a determination is made as to how many wave line segments will be required to update the waveform. The waveform line segments are lines drawn between two points on the waveform. The waveform is represented in two dimensions with the Y axis representing the value of the data source samples, and the X axis representing time. As stated above, the data samples received from the data source are operated upon by a decimation algorithm in order to reduce the number of data samples prior to display on the display device. After the representative data samples are selected, each selected data sample is assigned a pixel. As stated above, the waveform can be considered as comprising a plurality of line segments that interconnect two adjacent data samples such that each line segment has a delta-X of one.

At step 402, the number of line segments to be drawn is labeled as the "count" and is set equal to updateMultiplier multiplied by a constant labeled "defaultRepeatCount". As described above, updateMultiplier was calculated at step 310 of the method shown in FIG. 6 and is an integer value indicating the relationship between the number of data samples that would ideally be updated if the interrupt were serviced promptly, and the number of stored data samples that have not yet been updated. DefaultRepeatCount is a constant established for the particular user application and indicates the number of data samples that will ideally be updated when an interrupt is promptly serviced and there is no backlog of data samples to be updated. DefaultRepeatCount is related to the number of data samples that is expected to be received between promptly serviced interrupts, and is affected by the decimation algorithm chosen because it relates to the number of data samples that will typically be updated to the display screen, as opposed to the number that will be received and stored between interrupts. As can be seen from the foregoing, at step 402 the "count" is set equal to the number of data samples that will be displayed on the display device to update the waveform in response to the servicing of the current interrupt.

At step 404, the method calculates the display device location that is to be updated by the drawing of the next wave line segment. This calculation is performed by incrementing a variable x1 which indicates the column coordinate of the beginning point of the previously updated wave line segment. The method increments x1 at step 404 to establish the column coordinate for the beginning point of the next wave line segment to be drawn. When the variable x1 indicates the pixel-column at the right side of the drawing area, the incrementation at step 404 sets the variable x1 equal to zero, so that the drawing of the next wave line segment causes the waveform to wrap around to the left side of the display device.

At step 405, the method calculates the XY coordinates of the beginning and end points for the next line segment to be drawn, and sets a variable y'. The beginning point for the line segment is the pixel corresponding to the end point of the previously drawn line segment and has an X coordinate equal to x1 and a Y coordinate y1 that is equal to the value of the previously updated data sample which is displayed in that column.

The end point for the new line segment to be drawn has a Y coordinate y2 defined by the data sample currently being updated, and an X coordinate x2 that is equal to x1 plus one. The variable y' is set equal to the Y coordinate of the end point of the line segment for reasons that are described below.

After the XY coordinates are determined for the beginning and end points of the line segment to be drawn, the method proceeds to step 406 wherein a determination is made as to whether the Y coordinates for the beginning and end points of the line segment are equal. A determination that the Y coordinates are equal indicates that the line segment to be drawn is a horizontal segment which is treated as a special case. Therefore, when it is determined at step 406 that the Y coordinates of the beginning and end points of the line segment are equal, the method proceeds to step 408 wherein the variable y' is incremented by one. Incrementing y' causes the intermediate color antialiasing lines to be drawn in a way that has been found to most effectively smooth the appearance of the waveform. A horizontal line is a special case of a line segment because it does not involve a stair-step transition. Human factors experimentation has indicated that the smoothest looking waveform is generated when a one-pixel wide horizontal line is drawn in the intermediate color immediately adjacent each horizontal line segment of the waveform. Therefore, in order to facilitate the drawing of such an intermediate colored line, y' is set equal to the Y coordinate of the end point plus one at step 408 so that when the antialiasing line segments are drawn in the steps discussed below, a one-pixel wide intermediate color line will be drawn above each horizontal line segment. Alternatively, y' can be set equal to the Y coordinate of the end point minus one at step 408 so that when the antialiasing line segments are drawn in the steps discussed below, a one-pixel wide intermediate color line will be drawn below each horizontal line segment.

At step 410, the two antialiasing line segments are drawn. As described above, in this embodiment of the invention the X Windows line drawing command is used and is called twice to draw two vertical one-pixel wide lines in the intermediate color. The first antialiasing line is drawn between the beginning point of the wave line segment (x1, y1) and a pixel having the coordinates (x1, y'). Generally, y' will be equal to y2 which is the row coordinate of the end point of the wave line segment. However, when the wave line segment is horizontal, y' will equal y2 plus one. The second antialiasing line is drawn between a pixel having the coordinates (x2, y1), and a pixel having the coordinates (x2, y').

After the antialiasing line segments have been drawn, the method proceeds to step 412 wherein the line segment for the waveform is drawn in the foreground color between the beginning and end points of the wave line segment. As stated above, this line segment is drawn using the X Windows line drawing command so that the X server will determine where the midpoint transition of the line segment occurs from the pixel column including the beginning point to the pixel column including the end point.

After the waveform line segment is drawn, the method proceeds to step 414 wherein the count is decremented. Thereafter, the method proceeds to step 416 wherein a determination is made as to whether the count has a value greater than zero. When it is determined that the count is greater than zero, the method returns to step 404 wherein the beginning and end points for the next line segment are calculated. In this manner, the method iteratively draws line segments to update the waveform until it is determined at step 416 that the count is not greater than zero. When it is determined at step 416 that the count is not greater than zero, the updating of the waveform in response to the most recently serviced interrupt has been completed and the method returns to step 316 of the method shown in FIG. 6.

Although the above-described antialiasing methods have been described herein as being specifically implemented using X Windows commands, it should be understood that the present invention can also be used with other standard graphics drawing packages. Furthermore, the antialiasing methods of the present invention are not limited to use with standard graphics drawing packages. The antialiasing methods of the present invention can also be implemented in proprietary systems in order to simplify the manner in which waveforms are drawn.

As stated above, the waveform update scheduler of the present invention enables monitoring systems to be implemented with real-time, as well as non-real time, operating systems. Prior art real-time monitoring systems typically operate in a lock-step manner whereby the waveform is updated at consistent intervals. In order to operate in this manner, interrupt requests for updating the waveform are given high priority so that they are promptly serviced by the operating system. As a result, the processor is repeatedly interrupted from other processing tasks in order to update the waveform.

The waveform update scheduler of the present invention can be used with real-time monitoring systems to provide flexibility in the manner in which interrupts for updating the waveform are serviced. When the waveform update scheduler of the present invention is used in a real-time operating system, the interrupts for updating the waveform are not given as high a priority because they need not be serviced as promptly as in prior art monitoring systems. As a result, the processing of high priority tasks is not repeatedly interrupted to service waveform update interrupts. The added flexibility provided by the wave-update scheduler of the present invention allows real-time monitoring systems to operate more efficiently.

It should be understood that various changes and modifications of the embodiments shown in the drawings may be made within the scope of this invention. Thus, it is intended that all matter contained in the above description and shown in the accompanying drawings shall be interpreted and illustrative and not in a limiting sense.

What is claimed is:

1. A method for operating a monitoring system that displays a waveform representing a time-varying characteristic of a data source, the monitoring system receiving data samples from the data source at a data sample frequency, the monitoring system including a processor and a memory, the processor executing an operating system, the monitoring system further including a display device having a plurality of pixels, the display device displaying the waveform as a fixed wave with an erase bar moving across the display screen to update the waveform, the method comprising the steps of:

requesting that the operating system service an interrupt after an interrupt time period has lapsed;

storing the received data samples in the memory;

determining a maximum number of stored data samples that will be used to update the waveform at the servicing of the interrupt;

when the requested interrupt is serviced, determining whether the number of stored data samples exceeds the maximum number; and updating the waveform based on the stored data samples, including the step of;

updating the waveform based on only the maximum number of stored data samples when the number of stored data samples exceeds the maximum number.

2. A method as recited in claim 1 wherein the number of data samples received during the interrupt time period when the interrupt is serviced precisely at the requested time constitutes an ideal number of data samples upon which to base the waveform update at the servicing of each interrupt, and wherein the step of updating the waveform based on the stored data samples includes the step of updating the waveform based on a whole number multiple of the ideal number of data samples.

3. A method as recited in claim 1 wherein the step of determining the maximum number of stored data samples includes the step of establishing the maximum number to be equal to twice the number of data samples received from the data source during the interrupt time period when the interrupt is serviced precisely when requested.

4. A method as recited in claim 1 wherein the operating system is a non-real time operating system.

5. A method as recited in claim 1 wherein the step of determining the maximum number of stored data samples includes the step of establishing the maximum number so that the erase bar maintains an appearance of substantially constant velocity as the waveform is updated.

6. A method as recited in claim 1 including the step of selecting the interrupt time period to be a whole number multiple of the data sample frequency.

7. A method as recited in claim 1 including the steps of:

determining a difference between the time at which the interrupt was requested to be serviced and the time at which it was actually serviced, the difference indicating an interrupt lag time;

reducing the requested interrupt time period by an amount based upon the interrupt lag time; and following the step of updating the waveform, returning to the step of requesting that the operating system service an interrupt after the expiration of the reduced interrupt time period.

8. A method as recited in claim 7 including the step of determining the time at which a next data sample to be updated was received, and wherein the step of reducing the requested interrupt time period based upon the interrupt lag time includes the steps of:

determining an actual interrupt time period indicating an amount of time elapsed between the time the interrupt is serviced and the time at which the next data sample to be updated was received;

dividing the actual interrupt time period by the requested interrupt time period to generate a quotient and a remainder; and reducing the interrupt time period by the remainder.

9. A method as recited in claim 7 including the step of inhibiting the performance of the step of reducing the requested interrupt time period when the number of stored data samples exceeds the maximum number.

10. A method as recited in claim 7 wherein the step of updating the waveform based on the maximum number of data samples includes the step of identifying the next stored data sample to be updated, and wherein the step of determining whether the number of stored data samples exceeds the maximum number includes the steps of:

determining a predetermined time period during which the maximum number of data samples will be received from the data source;

determining the time at which the next data sample to be updated was received;

determining the time at which the last data sample was received before the servicing of the interrupt; and determining whether the time period elapsed between the receipt of the next data sample to be updated and the most recently received data sample exceeds the predetermined time period.

11. A method as recited in claim 7 wherein the monitoring system includes a graphics drawing package to draw the waveform on the display device, the display device pixels being arranged in an array, the array including a plurality of rows and columns, the graphics drawing package having a line drawing primitive which draws lines between two selected pixels, and wherein the step of updating the waveform includes the steps of:

selecting foreground, background and intermediate pixel colors;

determining a plurality of interconnected wave line segments that form the waveform, each wave line segment extending between first and second end pixels, the end pixels being located in adjacent pixel columns, the first end pixel having column and row coordinates indicating a position of the first end pixel on the display device, the second end pixel having column and row coordinates indicating a position of the second end pixel on the display device; and drawing each wave line segment of the waveform, the drawing of each wave line segment including the steps of;

calling the line drawing primitive to draw, in the intermediate color, a first line between the first end pixel of the wave line segment and a pixel having a column coordinate equal to the column coordinate of the first end pixel, and a row coordinate equal to the row coordinate of the second end pixel;

calling the line drawing primitive to draw, in the intermediate color, a second line between the second end pixel of the wave line segment and a pixel having a column coordinate equal to the column coordinate of the second end pixel, and a row coordinate equal to the row coordinate of the first end pixel; and calling the line drawing primitive to draw, in the foreground color, a third line between the first and second end pixels of the wave line segment.

12. A method as recited in claim 1 wherein the operating system is UNIX and wherein the step of requesting that the operating system service an interrupt includes the step of setting the UNIX select function timer equal to the requested interrupt time period.

13. A method as recited in claim 1 wherein the step of updating the waveform based on the maximum number of data samples includes the step of identifying the next stored data sample to be updated, and wherein the step of determining whether the number of stored data samples exceeds the maximum amount includes the steps of:

- establishing a predetermined time period during which the maximum number of data samples will be received from the data source;
- determining the time at which the next data sample to be updated was received;
- determining the time at which the last data sample was received before the servicing of the interrupt; and
- determining whether the time period elapsed between the receipt of the next data sample to be updated and the most recently received data sample exceeds the predetermined time period.

14. A method as recited in claim 1 wherein the monitoring system includes a graphics drawing package to draw the waveform on the display device, the display device pixels being arranged in an array, the array including a plurality of rows and columns, the graphics drawing package having a line drawing primitive which draws lines between two selected pixels, and wherein the step of updating the waveform includes the steps of:

- selecting foreground, background and intermediate pixel colors;
- determining a plurality of interconnected wave line segments that form the waveform, each wave line segment extending between first and second end pixels, the end pixels being located in adjacent pixel columns, the first end pixel having column and row coordinates indicating a position of the first end pixel on the display device, the second end pixel having column and row coordinates indicating a position of the second end pixel on the display device; and
- drawing each wave line segment of the waveform, the drawing of each wave line segment including the steps of:
  - calling the line drawing primitive to draw, in the intermediate color, a first line between the first end pixel of the wave line segment and a pixel having a column coordinate equal to the column coordinate of the first end pixel, and a row coordinate equal to the row coordinate of the second end pixel;
  - calling the line drawing primitive to draw, in the intermediate color, a second line between the second end pixel of the wave line segment and a pixel having a column coordinate equal to the column coordinate of the second end pixel, and a row coordinate equal to the row coordinate of the first end pixel; and
  - calling the line drawing primitive to draw, in the foreground color, a third line between the first and second end pixels of the wave line segment.

15. A method for scheduling waveform updates in a monitoring system that displays a waveform representing a time-varying characteristic of a data source, the monitoring system receiving data samples from the data source at a data sample frequency, the monitoring system including a processor and a memory, the processor executing an operating system, the monitoring system further including a display device that displays the waveform as a fixed wave with an erase bar moving across the display device to udpate the waveform, the method comprising the steps of:

- determining an ideal interrupt time period and a corresponding ideal number of data samples, the ideal interrupt time period indicating a time period at which the waveform would ideally be updated to synchronize waveform updates with the data source, the ideal number of data samples indicating the number of data samples that will be received from the data source during the ideal interrupt time period;
- requesting that the operating system service an interrupt after the expiration of the ideal interrupt time period;
- storing the received data samples in the memory;
- when the interrupt is serviced, determining the time at which a next data sample to be updated was received;
- determining an update time period indicating the amount of time elapsed between the receipt of the next data sample to be updated and the servicing of the interrupt;
- updating the waveform based on the stored data samples including the step of updating the waveform based on more than the ideal number of data samples when the update time period is two or more times as long as the ideal interrupt time period;
- determining a difference between the time at which the interrupt was requested to be serviced and the time at which the interrupt was actually serviced, the difference indicating an interrupt lag period;
- reducing the requested interrupt time period by the lag time period; and
- returning to the step of requesting that an interrupt be serviced.

16. A method as recited in claim 15 including the steps of:

- inhibiting the performance of the step of reducing the requested interrupt time period when the waveform is updated with more than the ideal number of data samples.

17. A method for operating a monitoring system that displays a waveform representing a time-varying characteristic of a data source, the monitoring system receiving data samples from the data source at a data sample frequency, the monitoring system including a processor, a memory and a timer, the processor executing an operating system, the monitoring system further including a display device having a plurality of pixels, the display device displaying the waveform as a fixed wave with an erase bar moving across the display device to update the waveform, the method comprising the steps of:

- setting the timer equal to an ideal interrupt time period indicating a time period at which waveform updates would ideally be performed to synchronize the waveform updates with the receipt of the data samples;
- requesting that the operating system service an interrupt after the expiration of the timer;
- storing the received data samples in the memory;
- when the requested interrupt is serviced, updating the waveform based on at least some of the stored data samples;
- determining a difference between the time at which the interrupt was requested to be serviced and the time at which the interrupt was actually serviced, the difference indicating an interrupt lag time;
- setting the timer equal to the ideal interrupt time period minus a value based on the interrupt lag time; and returning to the step of requesting that the operating system service an interrupt.

18. A method as recited in claim 17 including the steps of:
   determining whether the interrupt lag period exceeds the ideal interrupt time period; and
   when the interrupt lag period exceeds the ideal interrupt time period, inhibiting the step of reducing the interrupt time period.

19. A method as recited in claim 17 wherein the step of reducing the requested interrupt time period includes the steps of:
   determining an elapsed interrupt time period indicating the amount of time elapsed between the requesting and servicing of the interrupt;
   dividing the elapsed interrupt time period by the ideal interrupt time period to generate a quotient and a remainder; and
   reducing the interrupt time period by the remainder.

20. A method as recited in claim 19 including the steps of:
   determining whether the quotient is greater than one; and when the quotient is greater than one, inhibiting the step of reducing the interrupt time period.

21. A method as recited in claim 17 wherein the monitoring system includes a graphics drawing package to draw the waveform on the display device, the display device pixels being arranged in an array, the array including a plurality of rows and columns, the graphics drawing package having a line drawing primitive which draws lines between two selected pixels, and wherein the step of updating the waveform includes the steps of:
   selecting foreground, background and intermediate pixel colors;
   determining a plurality of interconnected wave line segments that form the waveform, each wave line segment extending between first and second end pixels, the end pixels being located in adjacent pixel columns, the first end pixel having column and row coordinates indicating a position of the first end pixel on the display device, the second end pixel having column and row coordinates indicating a position of the second end pixel on the display device; and
   drawing each wave line segment of the waveform, the drawing of each wave line segment including the steps of;
      calling the line drawing primitive to draw, in the intermediate color, a first line between the first end pixel of the wave line segment and a pixel having a column coordinate equal to the column coordinate of the first end pixel, and a row coordinate equal to the row coordinate of the second end pixel;
      calling the line drawing primitive to draw, in the intermediate color, a second line between the second end pixel of the wave line segment and a pixel having a column coordinate equal to the column coordinate of the second end pixel, and a row coordinate equal to the row coordinate of the first end pixel; and
      calling the line drawing primitive to draw, in the foreground color, a third line between the first and second end pixels of the wave line segment.

22. An antialiasing method for drawing a waveform on a display device, the display device having an array of pixels, the array including a plurality of rows and columns, the method including the steps of:
   selecting background, foreground and intermediate pixel colors;
   determining a plurality of interconnected wave segments that form the waveform, each wave segment extending between first and second end pixels, the end pixels being located in adjacent pixel columns;
   drawing one-pixel wide waveform-lines between the first and second end pixels of each wave segment, the waveform lines being drawn in the foreground color, each waveform line having a midpoint wherein the waveform line switches columns from the column including the first end pixel of the waveform line to the column including the second end pixel of the waveform line; and
   drawing an antialiasing line segment in the intermediate color for at least one waveform line, the antialiasing line segment having the same midpoint as the at least one waveform line and creating a mirror image of the at least one waveform line.

23. An antialiasing method for controlling a graphics drawing package to draw a waveform on a display device, the display device having an array of pixels, the array including a plurality of rows and columns, the graphics drawing package having a line drawing primitive which draws lines between two selected pixels, the method including the steps of:
   selecting foreground, background and intermediate pixel colors;
   determining a plurality of interconnected wave line segments that form the waveform, each wave line segment extending between first and second end pixels, the end pixels being located in adjacent pixel columns, the first end pixel having column and row coordinates indicating a position of the first end pixel on the display device, the second end pixel having column and row coordinates indicating a position of the second end pixel on the display device; and
   drawing each wave line segment of the waveform, the drawing of each wave line segment including the steps of;
      calling the line drawing primitive to draw, in the intermediate color, a first line between the first end pixel of the wave line segment and a pixel having a column coordinate equal to the column coordinate of the first end pixel, and a row coordinate equal to the row coordinate of the second end pixel;
      calling the line drawing primitive to draw, in the intermediate color, a second line between the second end pixel of the wave line segment and a pixel having a column coordinate equal to the column coordinate of the second end pixel, and a row coordinate equal to the row coordinate of the first end pixel; and
      calling the line drawing primitive to draw, in the foreground color, a third line between the first and second end pixels of the wave line segment.

24. An antialiasing method as recited in claim 23 wherein the steps of calling the line drawing primitive to draw the first and second lines are performed before the step of calling the line drawing primitive to draw the third line.

25. An antialiasing method as recited in claim 23 wherein the steps of calling the line drawing primitive to draw the first, second and third lines each include the step of instructing the line drawing primitive to draw a one-pixel wide line.

26. An antialiasing method as recited in claim 23 wherein the step of selecting the foreground, background and intermediate colors includes the step of selecting the intermediate color so that its red, green and blue components are each linearly halfway between the red, green and blue components of the foreground and background colors.

27. An antialiasing method as recited in claim 23 wherein the step of drawing the waveform includes the steps of:
- determining whether any wave line segments are horizontal; and
- calling the line drawing primitive to draw a one-pixel wide horizontal line in the intermediate color immediately adjacent any horizontal wave line segments.

28. A monitoring system for displaying a waveform representing a time-varying characteristic of a data source, the monitoring system comprising:
- a processor executing an operating system; means for displaying the waveform as a fixed wave with a moving erase bar to update the waveform;
- means for requesting that the operating system service an interrupt after an interrupt time period has lapsed;
- means for storing the received data samples; means for establishing a maximum number of stored data samples that will be used to update the waveform at the servicing of the interrupt;
- means for determining when the requested interrupt has been serviced;
- waveform update means for updating the waveform when the requested interrupt has been serviced, the waveform update means including;
- means for determining whether the number of stored data samples exceeds the maximum number; and
- means for updating the waveform based on only the maximum number of stored data samples when the number of stored data samples exceeds the maximum number.

29. A monitoring system as recited in claim 28 wherein said means for determining the maximum number of stored data samples includes means for establishing the maximum number so that the erase bar maintains an appearance of substantially constant velocity as the waveform is updated.

30. A monitoring system as recited in claim 28 further comprising:
- means for determining a difference between the time at which the interrupt was requested to be serviced and the time at which it was actually serviced, the difference indicating an interrupt lag time; and
- means for reducing the requested interrupt time period by an amount based upon the interrupt lag time.

31. A monitoring system for displaying a waveform representing a time-varying characteristic of a data source, the monitoring system comprising:
- a processor executing an operating system;
- means for displaying the waveform as a fixed wave with a moving erase bar to udpate the waveform;
- means for determining an ideal interrupt time period and a corresponding ideal number of data samples, the ideal interrupt time period indicating a time period at which the waveform would ideally be updated to synchronize waveform updates with the data source, the ideal number of data samples indicating the number of data samples that will be received from the data source during the ideal interrupt time period;
- means for requesting that the operating system service an interrupt after the expiration of the ideal interrupt time period;
- means for storing the received data samples;
- means for determining when the interrupt has been serviced;
- means for determining a difference between the time at which the interrupt was requested to be serviced and the time at which the interrupt was actually serviced, the difference indicating an interrupt lag period; and
- means for reducing the requested interrupt time period by the lag time period; and
- waveform update means for updating the waveform when the interrupt has been serviced, the waveform update means including;
  - means for determining the time at which a next data sample to be updated was received;
  - means for determining an update time period indicating the amount of time elapsed between the receipt of the next data sample to be updated and the servicing of the interrupt; and
  - means for updating the waveform based on more than the ideal number of data samples when the update time period is two or more times as long as the ideal interrupt time period.

32. A monitoring system for displaying a waveform representing a time-varying characteristic of a data source, the monitoring system receiving data samples from the data source at a data source frequency, the monitoring system comprising:
- a processor executing an operating system;
- means for displaying the waveform as a fixed wave with a moving erase bar to update the waveform;
- a timer for storing an interrupt time period;
- means for setting the timer equal to an ideal interrupt time period indicating a time period at which waveform updates would ideally be performed to synchronize the waveform updates with the receipt of the data samples;
- means for requesting that the operating system service an interrupt after the expiration of the timer;
- means for storing the received data samples;
- means for determining when the requested interrupt has been serviced and when the requested interrupt has been serviced, for updating the waveform based on at least some of the stored data samples;
- means for determining a difference between the time at which the interrupt was requested to be serviced and the time at which the interrupt was actually serviced, the difference indicating an interrupt lag time; and
- means for reducing the interrupt time period by a value based on the interrupt lag time.

33. An apparatus for drawing a waveform on a display device, the display device having an array of pixels, the array including a plurality of rows and columns, the apparatus comprising:
- means for selecting background, foreground and intermediate pixel colors;
- means for determining a plurality of interconnected wave segments that form the waveform, each wave segment extending between first and second end pixels, the end pixels being located in adjacent pixel columns;

means for drawing one-pixel wide waveform lines between the first and second end pixels of each wave segment, the waveform lines being drawn in the foreground color, each waveform line having a midpoint wherein the waveform line switches columns from the column including the first end pixel of the waveform line to the column including the second end pixel of the waveform line; and means for drawing an antialiasing line segment in the intermediate color for at least one waveform line, the antialiasing line segment having the same midpoint as the at least one waveform line and creating a mirror image of the at least one waveform line.

34. An apparatus for controlling a graphics drawing package to draw a waveform on a display device, the display device having an array of pixels, the array including a plurality of rows and columns, the graphics drawing package having a line drawing primitive which draws lines between two selected pixels, the method including the steps of:

means for selecting foreground, background and intermediate pixel colors;

means for determining a plurality of interconnected wave line segments that form the waveform, each wave line segment extending between first and second end pixels, the end pixels being located in adjacent pixel columns, the first end pixel having column and row coordinates indicating a position of the first end pixel on the display device, the second end pixel having column and row coordinates indicating a position of the second end pixel on the display device; and drawing means for drawing each wave line segment of the waveform, the drawing means including;

means for calling the line drawing primitive to draw, in the intermediate color, a first line between the first end pixel of the wave line segment and a pixel having a column coordinate equal to the column coordinate of the first end pixel, and a row coordinate equal to the row coordinate of the second end pixel;

means for calling the line drawing primitive to draw, in the intermediate color, a second line between the second end pixel of the wave line segment and a pixel having a column coordinate equal to the column coordinate of the second end pixel, and a row coordinate equal to the row coordinate of the first end pixel; and means for calling the line drawing primitive to draw, in the foreground color, a third line between the first and second end pixels of the wave line segment.

35. An antialiasing method for controlling a graphics drawing package to draw a waveform on a display device, the display device having an array of pixels, the array including a plurality of rows and columns, the graphics drawing package having a line drawing primitive which draws lines between two selected pixels, the method including the steps of:

selecting foreground, background and intermediate pixel colors;

determining a plurality of interconnected wave line segments that form the waveform, each wave line segment extending between first and second end pixels, the end pixels being located in adjacent pixel columns, the first end pixel having column and row coordinates indicating a position of the first end pixel on the display device, the second end pixel having column and row coordinates indicating a position of the second end pixel on the display device; and drawing each wave line segment of the waveform, the drawing of each wave line segment including the steps of;

calling the line drawing primitive to draw, in the intermediate color, a first line between the first and second end pixels of the wave line segment; and calling the line drawing primitive to draw, in the foreground color, a second line between the first and second end pixels of the wave line segment.

36. An antialiasing method as recited in claim 35 wherein the step of calling the line drawing primitive to draw the first line includes the step of instructing the line drawing primitive to draw a line having a width of more than one pixel.

37. An antialiasing method as recited in claim 36 wherein the step of calling the line drawing primitive to draw the first line is performed before the step of calling the line drawing primitive to draw the second line.

38. An antialiasing method as recited in claim 37 wherein the step of calling the line drawing primitive to draw the second line includes the step of instructing the line drawing primitive to draw a line having a width that is less than the width of the first line.

* * * * *